(12) United States Patent
Silva et al.

(10) Patent No.: US 10,478,237 B2
(45) Date of Patent: Nov. 19, 2019

(54) ORTHOPEDIC BONE PLATE SYSTEM

(71) Applicant: OsteoCertus, LLC, Pembroke Pines, FL (US)

(72) Inventors: Cesar Silva, Pembroke Pines, FL (US); David Augusto Silva, Popayán (CO); Javier E. Castaneda, Miami, FL (US)

(73) Assignee: OsteoCertus, LLC, Pembroke Pines, FL (US)

( * ) Notice: Subject to any disclaimer, the term of this patent is extended or adjusted under 35 U.S.C. 154(b) by 236 days.

(21) Appl. No.: 15/335,162

(22) Filed: Oct. 26, 2016

(65) Prior Publication Data

US 2017/0189089 A1     Jul. 6, 2017

Related U.S. Application Data

(63) Continuation-in-part of application No. 14/987,425, filed on Jan. 4, 2016, now Pat. No. 10,258,402.

(51) Int. Cl.
*A61B 17/80* (2006.01)
*A61B 17/86* (2006.01)
(Continued)

(52) U.S. Cl.
CPC ........ *A61B 17/8085* (2013.01); *A61B 17/808* (2013.01); *A61B 17/8023* (2013.01);
(Continued)

(58) Field of Classification Search
CPC ............. A61B 17/888; A61B 17/8888; A61B 17/8863; A61B 17/8605; A61B 17/86;
(Continued)

(56) References Cited

U.S. PATENT DOCUMENTS 4,297,993 A * 11/1981 Harle ...................... A61B 17/80
606/70
5,002,544 A   3/1991 Klaue et al.
(Continued)

FOREIGN PATENT DOCUMENTS

FR           2812536 A1    2/2002
KR         101201603 B1   10/2011
(Continued)

OTHER PUBLICATIONS 1.5 mm LCP Modular Mini Fragment System. 1.5 mm instrument and implant modules. Technique Guide, SYNTHES, 2009.
(Continued)

*Primary Examiner* — Kevin T Truong
*Assistant Examiner* — Jessica Weiss
(74) *Attorney, Agent, or Firm* — Gordon & Jacobson, P.C.

(57) ABSTRACT

A bone plate has first and second sides, each with the same structure. The plate includes nodes separated by deformable bridges. Each node defines a screw hole, and wings extending laterally therefrom. The wings taper in thickness between the first and second sides. Screw holes are threaded into the nodes. Each of the first and second sides of the body define longitudinal channels in the nodes. The plate can be shaped to the bone by deformation at the bridges or removal of portions of the plate at bridges. A pair of benders, each with clamp bracket and clamping bolt threadedly coupled within a threaded hole of the bracket, is also provided for shaping the plate.

13 Claims, 23 Drawing Sheets

(51) Int. Cl.
*A61B 17/88* (2006.01)
*A61B 90/00* (2016.01)

(52) U.S. Cl.
CPC .......... *A61B 17/8057* (2013.01); *A61B 17/86* (2013.01); *A61B 17/8605* (2013.01); *A61B 17/8863* (2013.01); *A61B 17/8888* (2013.01); *A61B 17/888* (2013.01); *A61B 2090/037* (2016.02)

(58) Field of Classification Search
CPC .............. A61B 17/808; A61B 17/8057; A61B 17/8023; A61B 17/8085
USPC ...................................... 606/70–71, 280–299
See application file for complete search history.

(56) References Cited

U.S. PATENT DOCUMENTS

| | | | |
|---|---|---|---|
| 5,053,036 A | 10/1991 | Perren et al. | |
| 5,151,103 A | 9/1992 | Tepic et al. | |
| 5,372,598 A * | 12/1994 | Luhr | A61B 17/8085 606/285 |
| 5,564,302 A | 10/1996 | Watrous | |
| 5,690,631 A * | 11/1997 | Duncan | A61B 17/8085 606/281 |
| 5,785,712 A * | 7/1998 | Runciman | A61B 17/8085 606/283 |
| 5,868,746 A | 2/1999 | Sarver | |
| 6,001,099 A | 12/1999 | Huebner | |
| 6,004,353 A | 12/1999 | Masini | |
| 6,309,393 B1 | 10/2001 | Tepic et al. | |
| 6,348,052 B1 | 2/2002 | Sammarco | |
| 6,454,770 B1 | 9/2002 | Klaue | |
| 7,189,237 B2 | 3/2007 | Huebner | |
| 7,704,251 B2 | 4/2010 | Huebner et al. | |
| 7,740,634 B2 | 6/2010 | Orbay et al. | |
| 7,771,433 B2 | 8/2010 | Orbay et al. | |
| 7,776,076 B2 * | 8/2010 | Grady, Jr. | A61B 17/8057 606/286 |
| 7,935,126 B2 | 5/2011 | Orbay et al. | |
| 8,080,010 B2 | 12/2011 | Schulz et al. | |
| 8,167,918 B2 | 5/2012 | Strnad et al. | |
| 8,172,886 B2 | 5/2012 | Castaneda et al. | |
| 8,231,663 B2 | 7/2012 | Kay et al. | |
| 8,292,898 B2 | 10/2012 | Castaneda et al. | |
| 8,419,745 B2 | 4/2013 | Sixto, Jr. et al. | |
| 8,518,088 B2 | 8/2013 | Castaneda et al. | |
| 8,568,462 B2 | 10/2013 | Sixto, Jr. et al. | |
| 8,632,574 B2 | 1/2014 | Kortenbach et al. | |
| 8,702,763 B2 | 4/2014 | Lin et al. | |
| 8,992,582 B1 | 3/2015 | Knoepfle et al. | |
| 2004/0092935 A1 | 5/2004 | Manderson | |
| 2004/0097936 A1 | 5/2004 | Ebid | |
| 2004/0220571 A1 * | 11/2004 | Assaker | A61B 17/7059 606/296 |
| 2005/0149026 A1 | 7/2005 | Butler et al. | |
| 2005/0273104 A1 * | 12/2005 | Oepen | A61B 17/8085 606/285 |
| 2006/0004362 A1 | 1/2006 | Patterson et al. | |
| 2008/0015591 A1 | 1/2008 | Castaneda et al. | |
| 2008/0221574 A1 | 9/2008 | Cavallazzi et al. | |
| 2009/0118768 A1 | 5/2009 | Sixto, Jr. | |
| 2009/0281543 A1 * | 11/2009 | Orbay | A61B 17/80 606/70 |
| 2009/0299369 A1 | 12/2009 | Orbay et al. | |
| 2009/0318979 A1 | 12/2009 | Raines | |
| 2010/0069966 A1 * | 3/2010 | Castaneda | A61B 17/1728 606/280 |
| 2010/0131012 A1 | 5/2010 | Ralph et al. | |
| 2011/0022049 A1 | 1/2011 | Huebner et al. | |
| 2011/0092981 A1 | 4/2011 | Ng et al. | |
| 2011/0144698 A1 | 6/2011 | Buchbinder et al. | |
| 2012/0065689 A1 | 3/2012 | Prasad et al. | |
| 2012/0109214 A1 | 5/2012 | Leither et al. | |
| 2013/0023938 A1 | 1/2013 | Huebner et al. | |
| 2013/0204307 A1 | 8/2013 | Castaneda et al. | |
| 2014/0000092 A1 | 1/2014 | Fritzinger et al. | |
| 2015/0073486 A1 | 3/2015 | Marotta | |
| 2016/0192970 A1 * | 7/2016 | Dayton | A61B 17/8085 606/281 |

FOREIGN PATENT DOCUMENTS

| | | | |
|---|---|---|---|
| WO | WO2014/074850 A1 | 5/2014 | |
| WO | WO2015/095126 A1 | 6/2015 | |

OTHER PUBLICATIONS

Graduated Stability Plates (GSP), Stryker, Leibinger Micro Implant Products, 2004.

Product Rationale & Surgical Technique, ALPS Total Foot System, Biomet Orthopedics, 2012.

Supplementary European Search Report of Application No. EP17736196 dated Aug. 1, 2019.

* cited by examiner

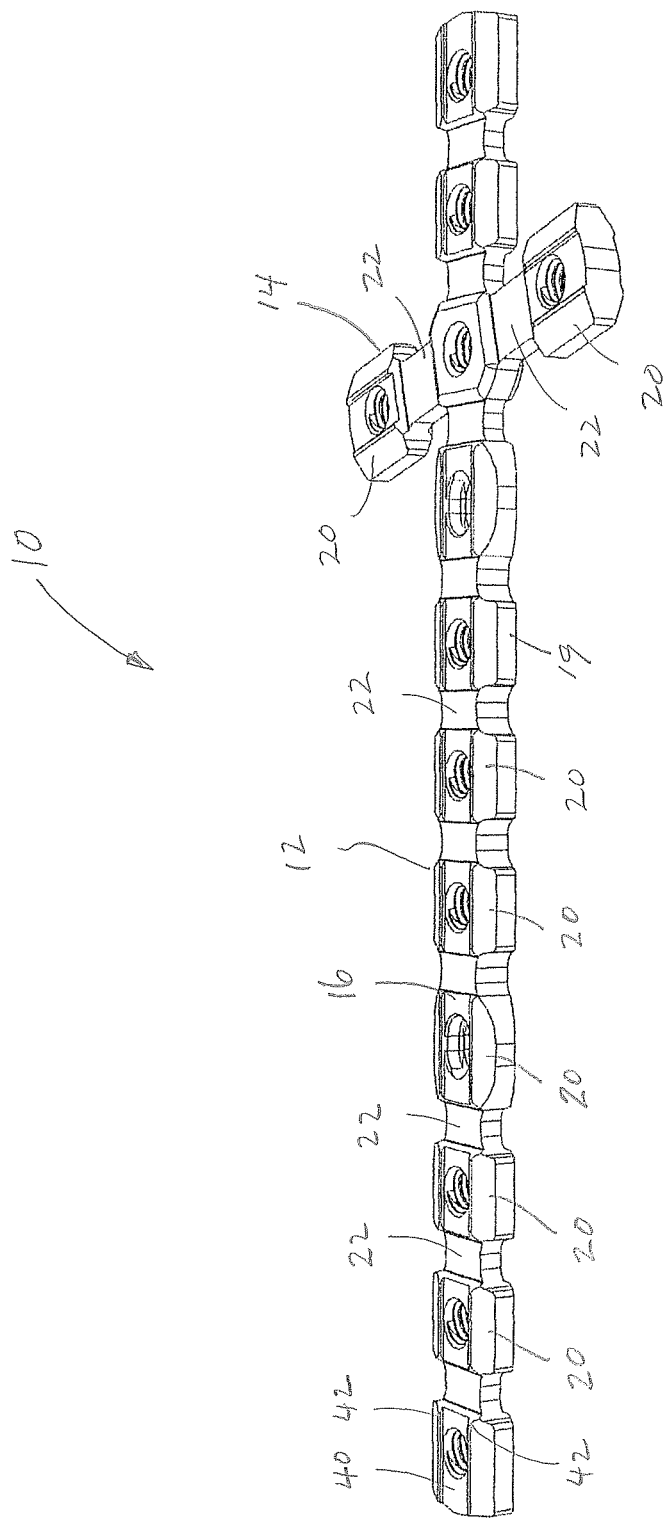

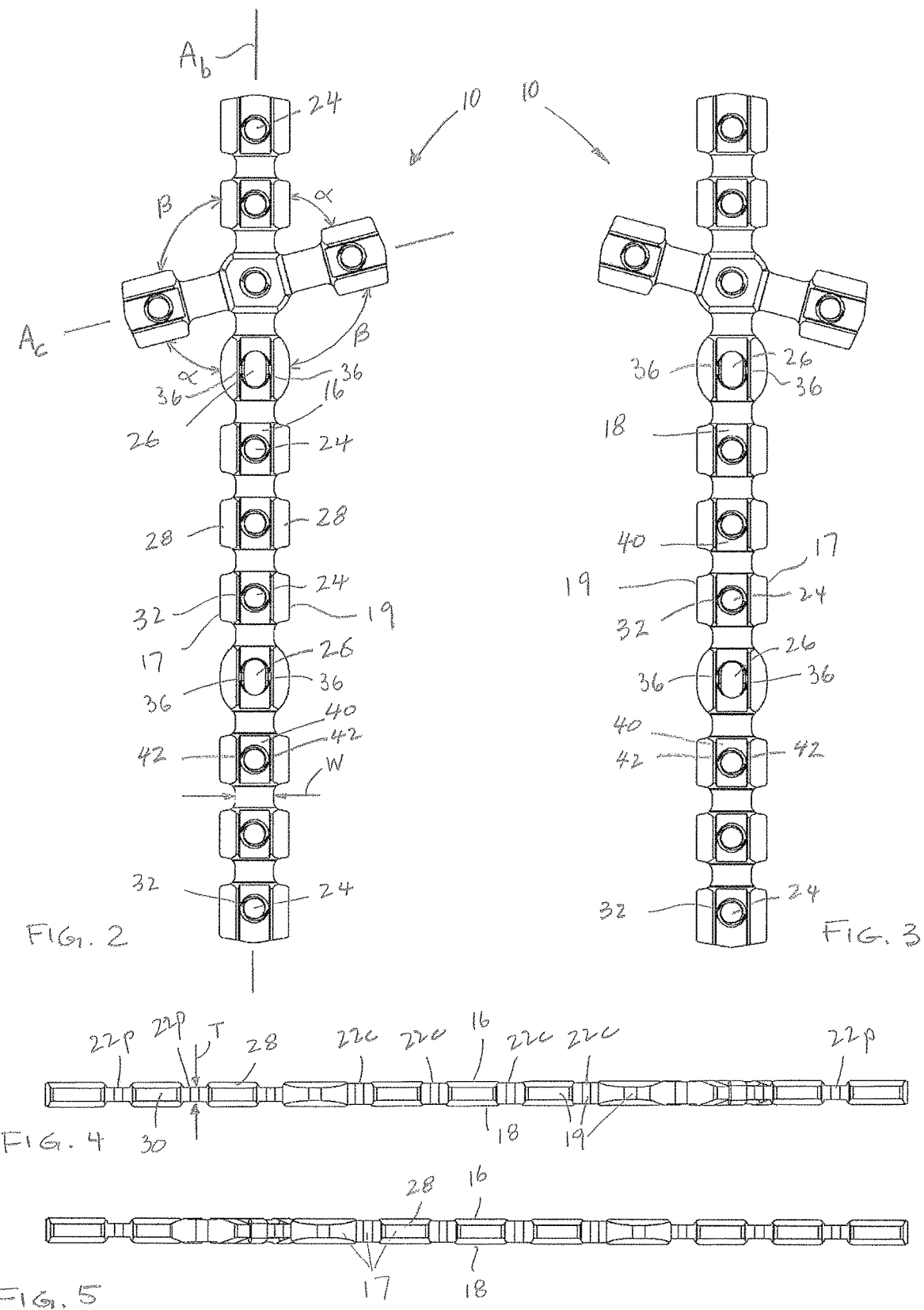

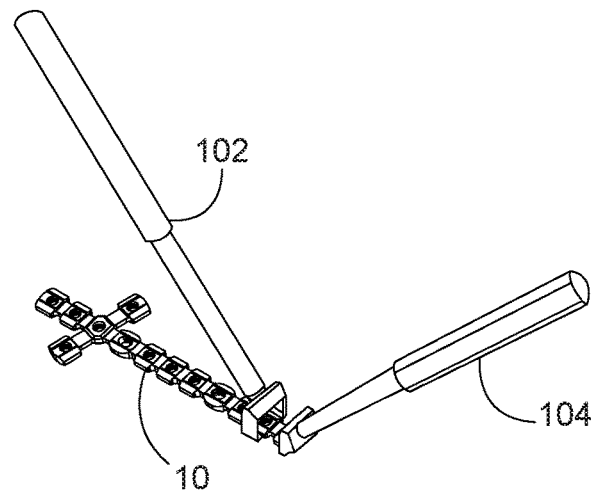 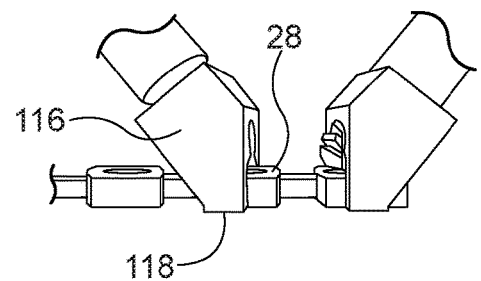
FIG. 18A  FIG. 18B
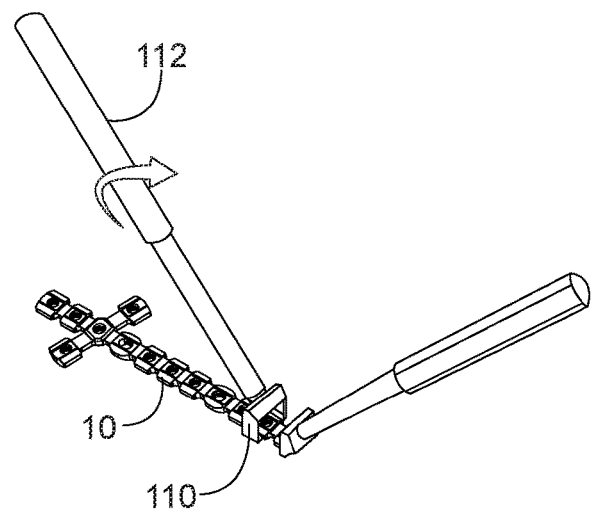 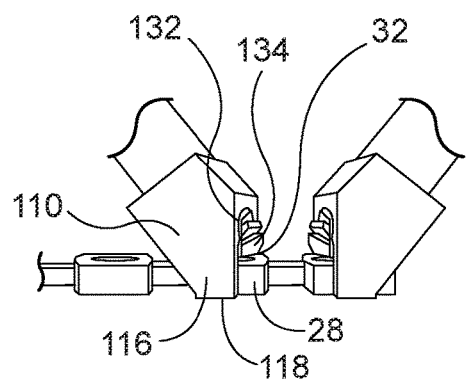
FIG. 19A  FIG. 19B

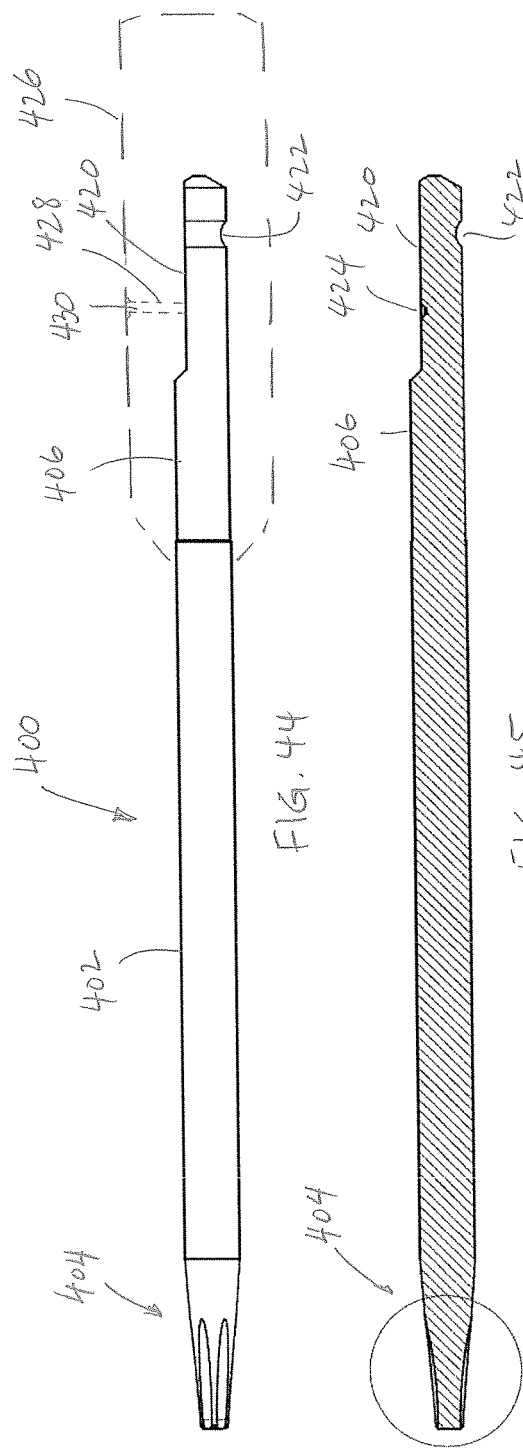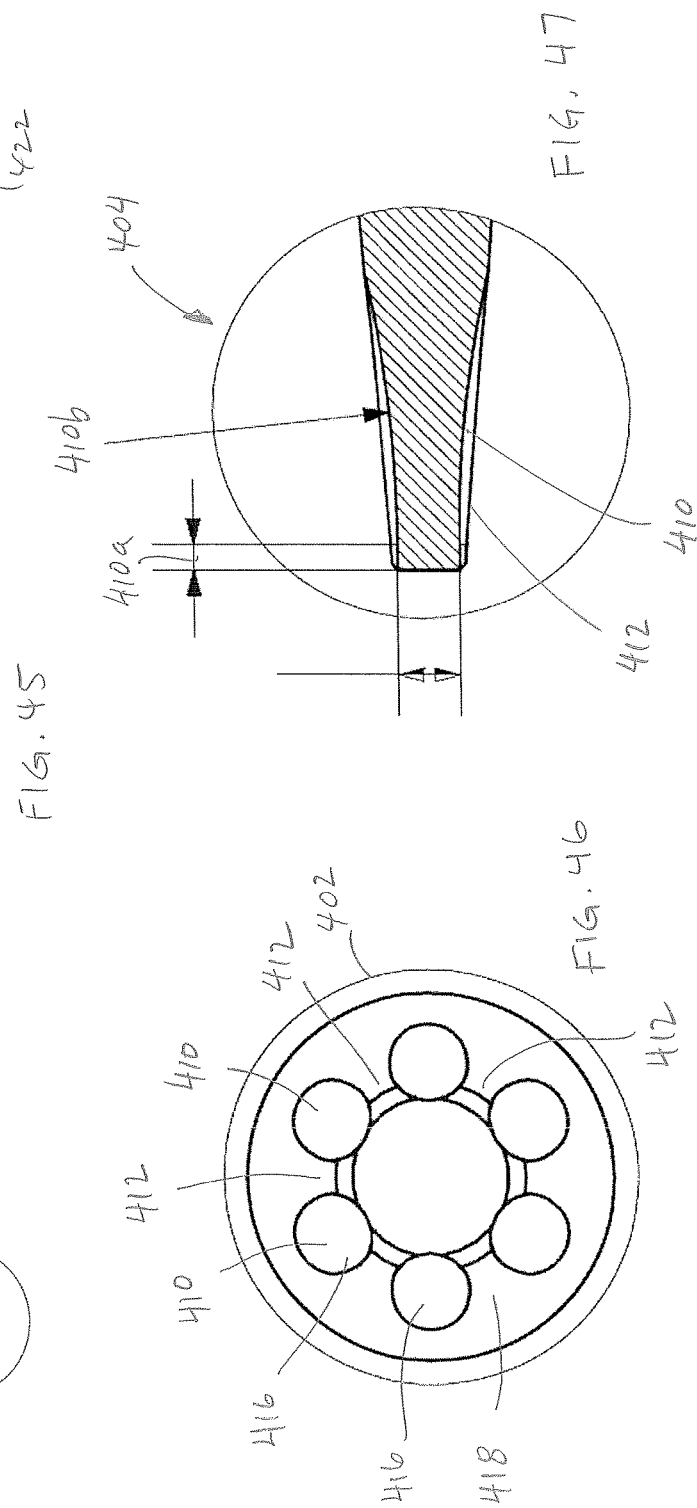

ORTHOPEDIC BONE PLATE SYSTEM

CROSS-REFERENCE TO RELATED APPLICATION

This application is a continuation-in-part of U.S. Ser. No. 14/987,425, filed Jan. 4, 2016, which is hereby incorporated by reference herein in its entirety.

BACKGROUND

1. Field

The present invention relates to surgery. More particularly, the invention relates to bone plates, instruments, and methods for internal orthopedic fixation in mammals.

2. State of the Art

Orthopedic plates are known for treating traumatic bone injuries in humans and other mammals. With respect to human treatment, significant development has been made in designing plates that are less of a general elongate form, but rather are more particularly adapted to the specific bones for which they are intended. That is, there has been a trend toward developing anatomical plates. In an anatomical plate, the bone-contacting surface of the plate closely fits the surface contours of the bone to which the plate is specifically adapted. These plates are generally provided in two versions of mirrored symmetry for use on the bones of the left and right sides of the body.

While good results have been reported with such anatomical plates, their use requires that treatment centers maintain a large inventory of different plates, each adapted for the different bones of the body, bones of different sizes, and the left and right sides of the body. The maintenance of such an extensive inventory can be costly, which is a significant disadvantage for treatment centers that may use certain plates with only a low frequency.

Further, while for a human population, the expense of a costly inventory often can be justified or required, animal populations do not benefit from such luxury. Veterinary surgical plates are often more basic than their human counterparts, of a general purpose, and not well adapted to the anatomical contours of the bone.

SUMMARY

Sets of two shapes of rigid, metal bone plates are provided in a system. The bone plates of each shape are provided in several sizes and can be adapted for treatment of many different types of bone fractures and bone sizes. The first shape plate is planar, in the form of a 't', and, in an embodiment, consists of a straight body and a cross arm. The second shape plate is planar and straight.

According to an aspect of the first shape bone plate, the cross arm extends transverse to the body at a non-orthogonal angle. The bone plate has a first side and a second side. According to another aspect of the bone plate, each of the first and second sides are adapted with same structure and contours such that each can be positioned against and in contact with the bone being treated, thereby providing treatment for bones on one lateral side of the body when the first side is positioned against the bone, and treatment for bones on the other lateral side of the body when the second side is positioned against a respective bone. As such, the plates have the same structure at their first and second sides.

More particularly, the body and cross arm of each plate include nodes separated by deformable bridges. The body portion defines a body axis extending centrally along the bridges of the body. The cross arm includes a cross axis extending centrally along the bridges of the cross arm. Each node defines a central screw hole, and wings extending laterally outward from the axis on which the node is situated. The wings taper in thickness between the first and second sides. The screw holes in a plurality of the nodes are preferably threaded, and in at least one node is preferably an elongate slot. The threaded screw holes all include an upper countersink.

The body and cross arm further define respective central longitudinal channels on each of the first and second sides of the plate in which the screw holes of the nodes are positioned. The channels have sides defining a pair of rails. When the first side of the plate is placed into contact with the bone, the rails seat against the bone and allow a convex bone to extend into the channels, and the channels at the second side define respective spaces in which screw heads of screws within the screw holes may be recessed. Similarly, when the second side of the plate is placed into contact with the bone, the rails on the second side seat against the bone, and the channels at the first side define respective spaces in which screw heads of screws within the screw holes may be recessed. The nodes at a more central location of the plate are stiffer and more resistant to deformation.

The straight plate in a preferred design has a particular arrangement of thirteen holes. From one end of the plate, the plate has a threaded circular hole, then an oblong hole, then two threaded circular holes, then an oblong hole, then three threaded circular holes, then an oblong hole, then two threaded circular holes, then an oblong hole, and finally a threaded circular hole. The straight second plate defines nodes, wing structures, and channels, as in the cross-arm first plate.

The plates may be shaped by removal of portions of the plate at bridges between the nodes. The removal can be performed with a cutting instrument or by reverse bending until breakage at a selected bridge. Specifically, the straight second plate can be bent towards its longitudinal center to break the plate into two plates: one with six holes and the other with seven holes, and each having threaded circular holes at their respective ends. The plates may be further shaped to the bone by plastic deformation of the plate at the bridges between the nodes.

In accord with another aspect of the system, a bending system is provided to bend the plates at the bridges between the nodes. The bending system includes first and second benders, each of preferably like structure and assembly. Each bender includes a clamp bracket and a handle. The bracket includes a body, an upper threaded hole in the body, and a pair of spaced-apart arms descending from the body, each terminating in a inwardly directed seat. The space between the seats at the lower ends of the arms is sufficient to be received vertically over a bridge of the plate but too small to accommodate vertical passage over the wings of a node. However, the space between the arms in relation to the wings allows the arms to be moved along the axis from a bridge to an adjacent node, with the lower end of the wings of the node engaging the seats. In a first embodiment of a bending system, the handle includes a proximal shaft and a distal threaded clamping bolt which is threadedly coupled within the threaded hole of the bracket and extends into the space between the arms. The end of the clamping bolt is convex and sized to seat against the countersink of a threaded screw hole. The first embodiment of the bending system is adapted to bend the plate out of plane. In a second embodiment of the bending system, the bracket includes lateral exterior slots along an upper portion thereof, and a bending arm is provided that engages within the slots.

In use, an appropriately sized bone plate is selected for a bone, such as a long bone or the pelvis. The orientation of the plate is selected, such that one of the first and second surfaces is identified and/or selected for placement against the bone. The plate is then reshaped as necessary and secured to the bone. The plate may be fully or partially reshaped before any attachment to the bone, or may be preliminarily attached to the bone and then reshaped and further secured.

More particularly, to reshape the plate at a bridge, a pair of benders are positioned on the plate at the two nodes on opposite sides of the bridge. Each bender is placed over a bridge and then slid into place on its respective node. Then the handle is rotated relative to the bracket to cause the clamping bolt to advance against the upper surface of the plate, at the countersink and without entering the threads of the screw hole. When the handle is rotated, the bracket is stably retained on the plate by the position of the arms about the wings of the node. The handle is rotated until the plate is clamped between the clamping bolt and the seats on the arms. Once each bender is coupled to its respective node, a relative force is applied between the benders to deform the bridge and thereby shape the plate.

The system also includes screws for securing the plate to the bone. In a preferred system, both locking screws and compression screws are provided. In addition, screws of different diameter and length are also provided for appropriate fixation and repair of the bone injury.

The system also includes a driver for picking up the screws and driving the screws through the plate and into the bone.

The system provides limited number of plate designs that accommodates left and right anatomies and which can also be customized in shape via removal of one or more nodes and bending along one or more bridges. The limited plate designs are readily adaptable into treatment even for those surgeons who have not had significant prior experience with anatomical or shapeable plates adapted for specific bones.

BRIEF DESCRIPTION OF THE DRAWINGS

FIG. 1 is a perspective view of a plate according to a system described herein.

FIG. 2 is a plan view of a first side of the plate of FIG. 1.

FIG. 3 is a plan view of a second side of the plate of FIG. 1.

FIG. 4 is an elevation view from the right side of the plate as oriented in FIG. 2.

FIG. 5 is an elevation view from the left side of the plate as oriented in FIG. 2.

FIG. 16A through 20B illustrate methods of bending plates of the system, with the 'A' figures showing the system in total, and the 'B' figures showing enlargements of respective portions in the 'A' figures.

FIG. 44 is a side elevation view of a screwdriver of the system.

FIG. 45 is a longitudinal section view of a shaft of the screwdriver of FIG. 44.

FIG. 46 is an enlarged distal end view of the shaft of the screwdriver of FIG. 44.

FIG. 47 is an enlarged longitudinal section view of the distal end of the shaft of the screwdriver of FIG. 44.

DETAILED DESCRIPTION OF THE PREFERRED EMBODIMENTS

Figure 6:
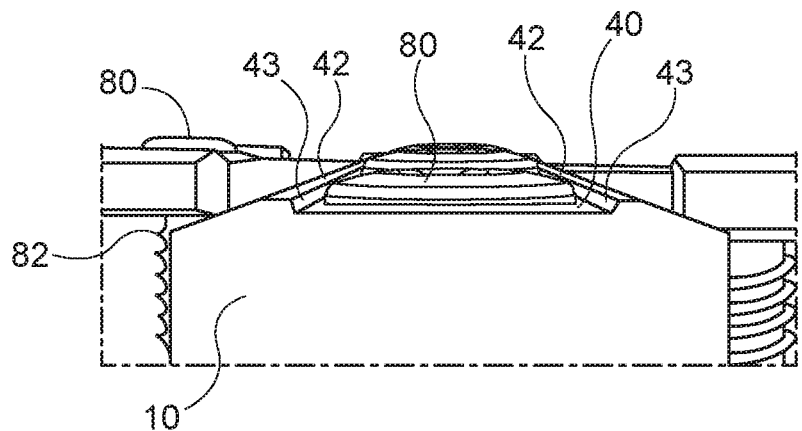
FIG. 6 is a cross sectional perspective view across a body portion of the plate, orthogonal to the longitudinal axis of the body portion.

In accord with the system herein, sets of bone plates of two different shapes are provided in a system. The bone plates of each shape are provided in several sizes and can be adapted for treatment of many different types of bone fractures and bone sizes.

Turning now to FIGS. 1 through 5, a first bone plate 10 is shown. The plate 10 is preferably made of metal, and has sufficient rigidity to provide stability to a broken bone. The bone plate 10 is in the form of a 't' and includes, and in embodiments consists of, a straight body 12 and a straight cross arm 14. The cross arm 14 extends transverse to the body 12 at a non-orthogonal angle, preferably forming two a angles of 75±10°, and two respectively supplementary angles β of 105°±10°, giving the plate a bilaterally asymmetric design.

The bone plate 10 extends in a plane, and has a first side 16, a second side 18, and lateral sides 17, 19 extending between the first and second sides. According to another aspect of the bone plate 10, each of the first and second sides 16, 18 are adapted with the same structure and contours such that each can be positioned against and in contact with the bone being treated, thereby providing treatment for bones on one lateral side of the body when the first side is oriented as a bone contacting surface, and treatment for bones on the other lateral side of the body when the second side is positioned against a respective bone.

More particularly, each of the body 12 and cross arm 14 of the plate 10 includes a linear arrangement of alternating nodes 20 and bridges 22. The body 12 defines a body axis $A_b$ extending centrally along the bridges 22 of the body. The cross arm 14 includes a cross axis $A_c$ extending centrally along the bridges 22 of the cross arm 14. The bridges 22 have a width W extends orthogonal to the respective axis $A_b$, $A_c$ along which it lies, and a thickness T extending between the first and second sides 16, 18. The bridges 22 have a reduced area moment of inertia relative to the nodes 20 such that the bridges have an increased propensity to bending deformation relative to the nodes when a bending force is applied thereto. Also, the bridges 22 have reduced polar moment of inertia relative to the nodes 20 such that the bridges have an increased propensity to twisting deformation relative to the nodes when a torqueing force is applied thereto.

Each node 20 defines a central screw hole 24 or 26, and wings 28 extending laterally outward from the axis on which the node is situated. The wings 28 taper at a common first angle in thickness equally between the first and second sides 16, 18 such that the lateral ends 30 of the wings are thinner than the thickness of the node and are elevated relative to whichever of the first and second sides 16, 18 is the bone contacting surface of the bone plate 10. The screw holes 24, which are provided in a plurality of the nodes, are threaded and include countersinks 32 opening at each of the first and second sides 16, 18; i.e., at each of their ends. The screw holes 26 in two of the relatively longitudinally central nodes of the body 12 are elongate, preferably non-threaded, and define elongate slots. Elongate screw holes 26 include a pair of ledges 36 extending along the sides of the hole that are adapted to functionally either (i) be engaged by the threads on the threaded head of a locking screw and allow locking relative thereto, or (ii) act as a stop for the head of a compression screw. These features are described further below.

The body 12 and cross arm 14 further define respective central longitudinal channels 40 on each of the first and second sides 16, 18 of the plate in which the screw holes 24, 26 of the nodes 20 are positioned. The channels 40 have sides defining a pair of rails 42. When the first side 16 of the plate is made a bone-contacting side, the rails 42 of the first side seat against the bone and allow a convex bone portion to extend at least partially into the channel 40 thereat, and the opposing channel on the second side 18 defines respective spaces on the nodes in which screw heads 80 of screws 82 (FIG. 6) positioned within the screw holes 24 may be recessed. Similarly, when the second side 18 of the plate is placed is made the bone-contacting side and placed into contact with the bone, the rails on the second side seat against the bone, and the channel at the first side defines respective space in which screw heads of screws within the screw holes of the nodes may be recessed. The rails 42 have a beveled medial side 43 extending at an angle.

The bridges $22_c$ at a more central location of the plate 10; i.e., located between the nodes provided with the elongate screw slots 26, are thicker, stiffer and more resistant to deformation, whereas the relatively proximal, distal, and lateral (more peripheral) bridges $22_p$ are thinner and more susceptible to deformation (FIG. 4). The plate 10 may be shaped to the bone by plastic deformation of the plate at the bridges 22 between the nodes 20. More particularly, the thinner bridges $22_p$ are utilized for shaping, as described in more detail below.

Figure 10:
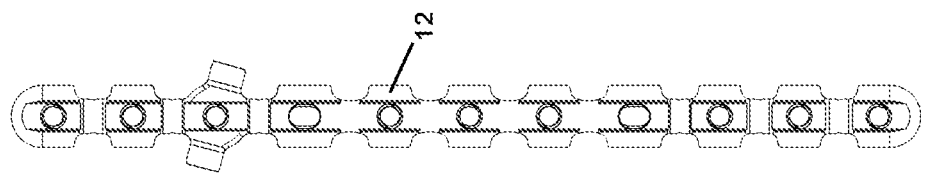

The plate may be further shaped by removal of peripheral portions of the plate at bridges 22 between the nodes. The removal can be performed with a suitable cutting instrument or by reverse bending until breakage at a selected bridge. FIGS. 7 through 10 show various exemplar plate shapes that can be formed by removal of peripheral portions of the plate, preferably about the intersection of the body 12 and cross arm 14. By way of example, the plate can be shaped into a slanted-'T' (FIG. 7), various one-armed shapes (FIGS. 8 and 9), and a straight plate (FIG. 10).

Figure 28:
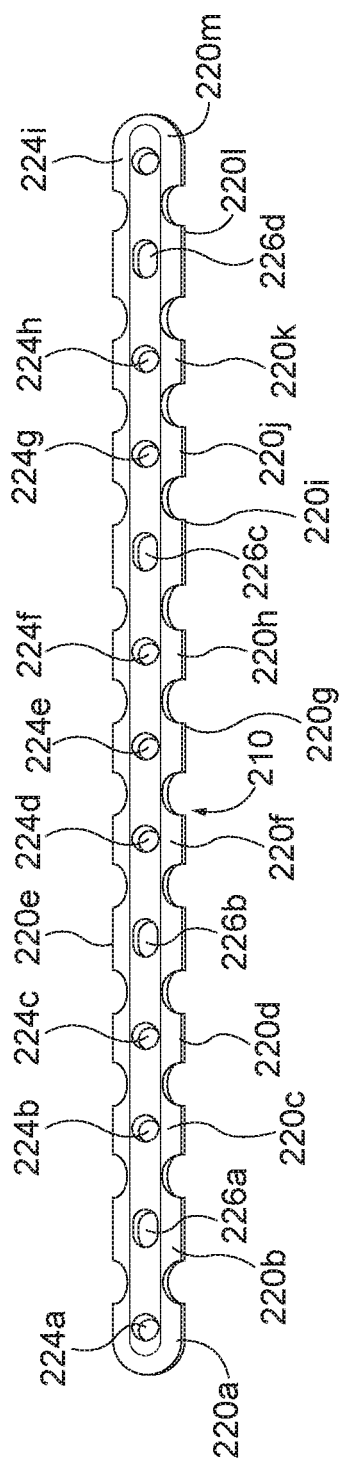
FIG. 28 is a perspective view of another plate according to the system described herein.

Turning now to FIG. 28, a second shape of bone plate 210 preferably provided with the system is already both planar and straight. As described above with respect to bone plate 10, each of the first and second sides of bone plate 210 are preferably adapted with the same structure and contours such that either surface of the plate may be positioned against the bone with equal effect. In addition, the plate 210 defines nodes, wing structures, rails, channels, and bridges of the same structure as in the cross-arm first plate 10. In one preferred design, each straight second plate 210 has a nodal arrangement with thirteen holes, including threaded circular holes and preferably non-threaded, elongate (in the direction of the longitudinal axis of the plate; i.e., non-circular, e.g., oval) holes that are preferably the same size, shape, and structure as holes 24, 26, describe above, so that common fasteners may be used with each. In this design, from one end of the bone plate 210, the plate has a first node 220a with a threaded circular hole 224a, then a second node 220b with an elongate hole 226a, then third and fourth nodes 220c, 220d with threaded circular holes 224b, 224c, then a fifth node 220e with elongate hole 226b, then sixth, seventh, and eighth nodes 220f, 220g, 220h with threaded circular holes 224d, 224e, 224f, then a ninth node 220i with an elongate hole 226c, then tenth and eleventh nodes 220j, 220k with threaded circular holes 224g, 224h, then a twelfth node 220l with an elongate hole 226d, and finally a thirteenth node 220m with a threaded circular hole 224i.

The plate 210 can be broken at a selected bridge to separate the plate 210 into two or more plate portions. By way of example, the plate can be subject to reverse bending at a central bridge between nodes 220f and 220g to provide a first plate portion having four nodes with threaded circular holes (220a, 220c, 220d, 220f) and two nodes with non-circular holes (220b, 220e), and a second plate portion having five nodes with threaded circular holes (220g, 220h, 220j, 220k, 220m) and two nodes with non-circular holes (220i, 220l).

Figure 11:
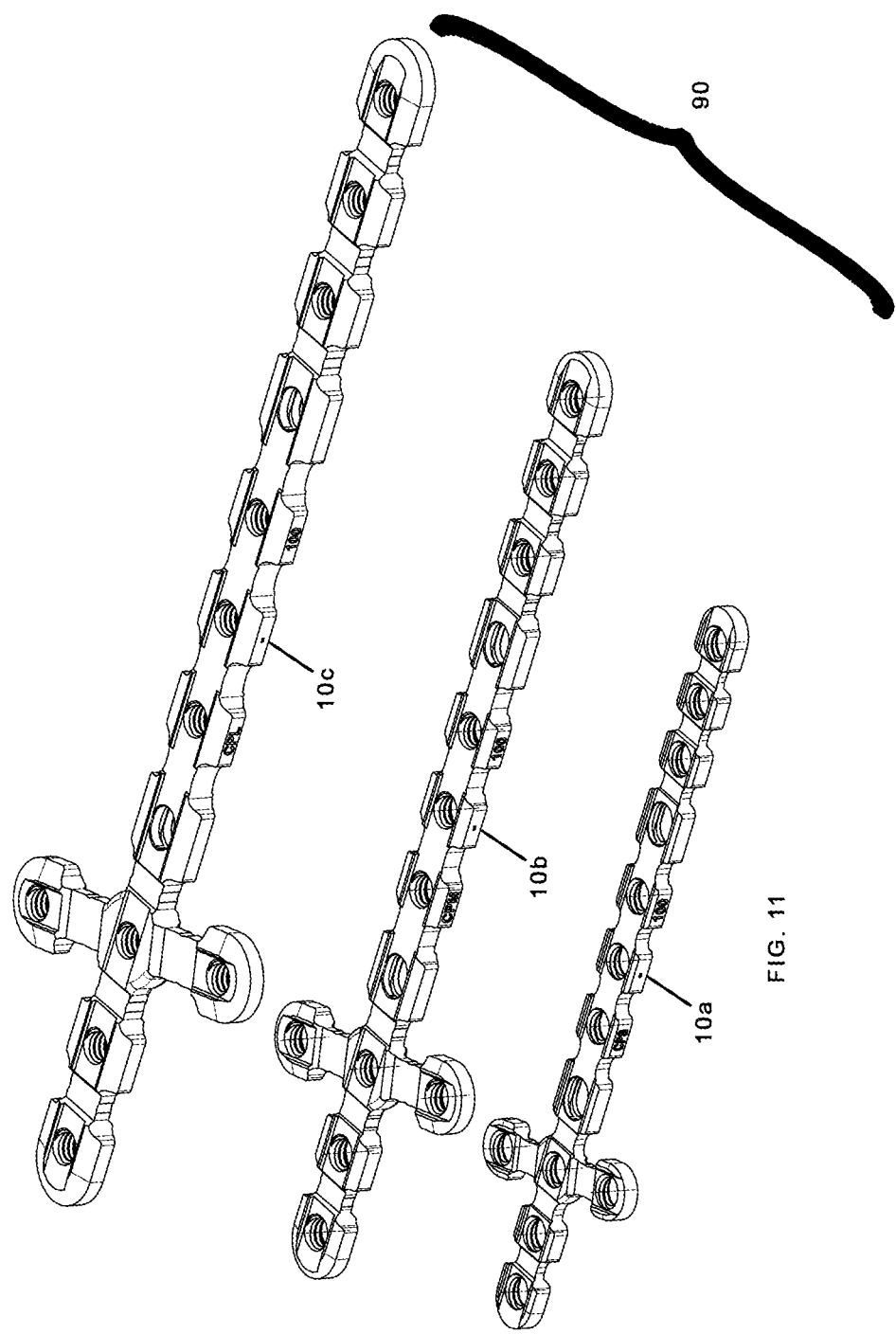
FIG. 11 is a perspective view of a set of plates of the type shown in FIG. 1.
Figure 29:
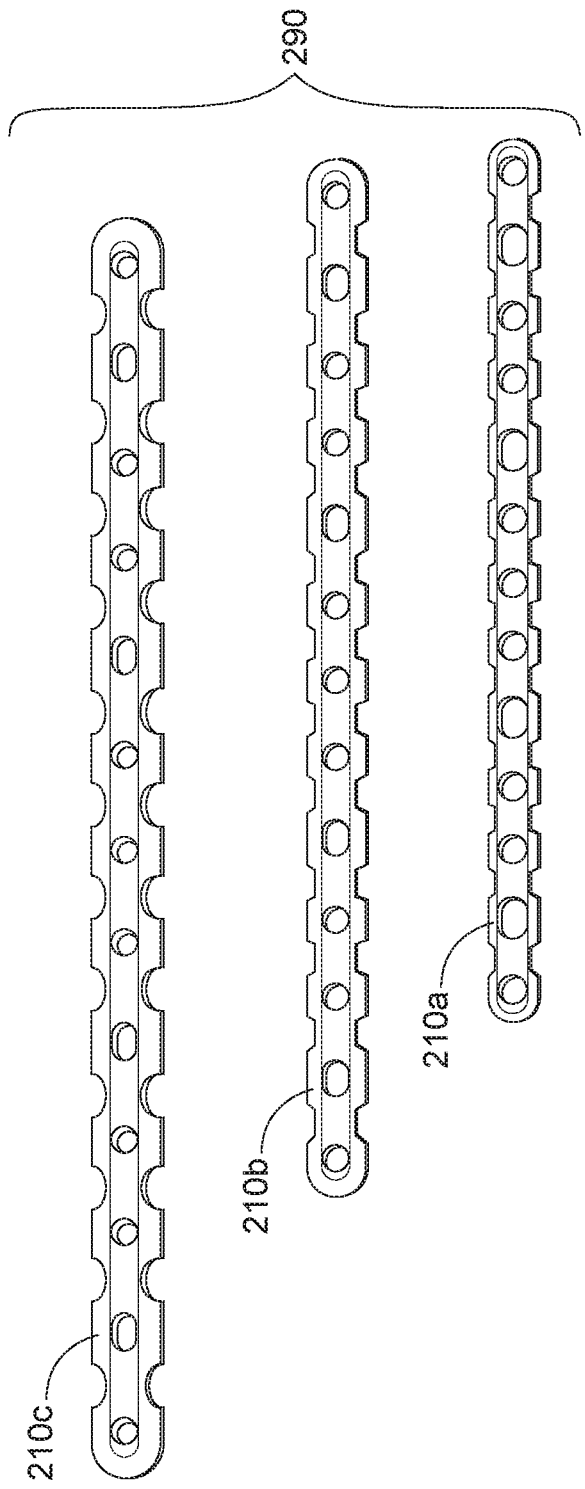
FIG. 29 is a perspective view of a set of plates of the type shown in FIG. 28.

Referring to FIG. 11, in accord with another aspect of the system, a limited set 90 of bone plates 10, each of like design but of a different size, are provided that can be adapted for treatment of many different types of bone fractures and bone sizes. The set preferably includes exactly three first plates, generally a relatively small size plate 10a, a relatively medium size plate 10b, and a relatively large size plate 10c, each for appropriate applications. Similarly, referring to FIG. 29, the system preferably includes a limited set 290 of straight bone plates 210, each of like design but of a different size, are provided that can be adapted for treatment of many different types of bone fractures and bone sizes. The set 290 preferably includes exactly three plates, generally a relatively small size plate 210a, a relatively medium size plate 210b, and a relatively large size plate 210c, each for appropriate applications. A fewer or greater number of plates can be provided in sets 90, 290, particularly depending on the population for which the plates are intended and their range of sizes. Such applications may be related to different size bones in the body of a patient, or bones in different patients of different sizes. While the plate can be used in a human population, the plates are particularly adapted for veterinary use, where the animals requiring treatment have a significant range in size between, e.g., small cats to large dogs. By way of example, the small plates 10*a*, 210*a* are sized to accommodate mammals of 5-15 kg, the medium plates 10*b*, 210*b* are sized to accommodate mammals of 15-25 kg, and the large plates 10*c*, 210*c* are sized to accommodate 25-40 kg, though usage of the plates on mammals of various sizes other than those indicated by example is certainly anticipated.

Figure 12:
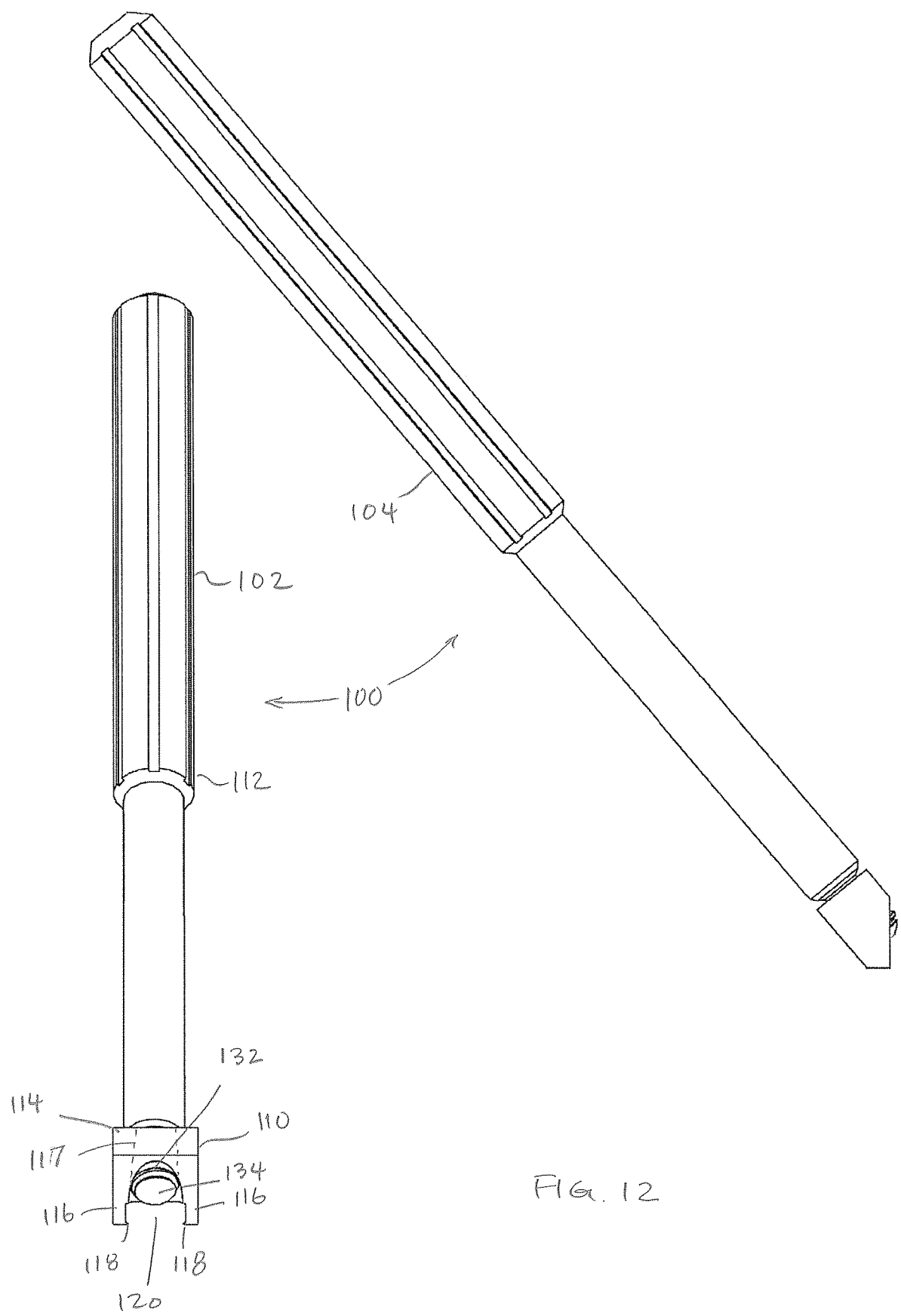
FIG. 12 shows a pair of plate benders, one in front view and one in side elevation view.
Figure 13:
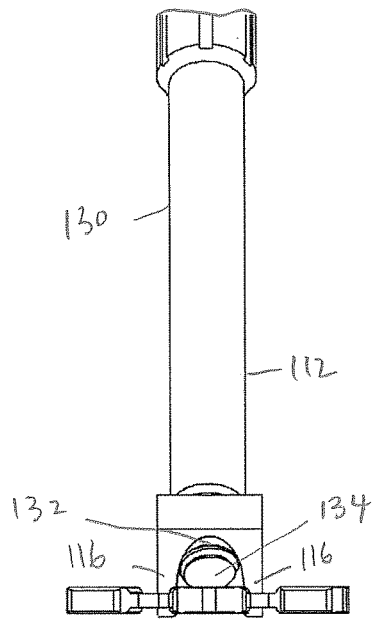
FIG. 13 shows, in a front view, a system of a plate bender coupled to a plate.
Figure 14:
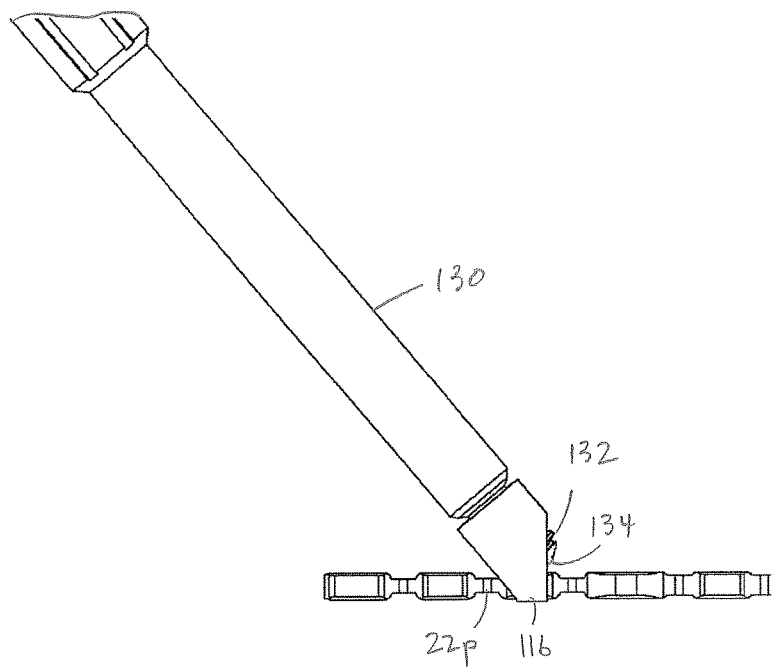
FIG. 14 shows, in a side elevation view, the system of FIG. 13.
Figure 15:
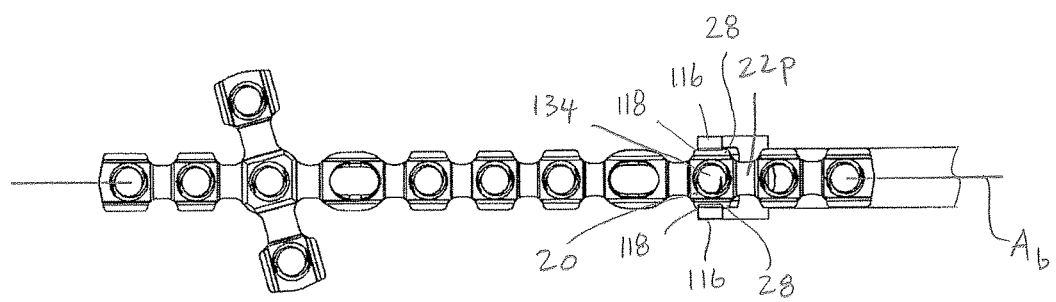
FIG. 15 shows, in a bottom view, the system of FIG. 13.

Turning now to FIG. 12, in accord with another aspect of the system, a bending system 100 is provided to bend the plate 10 out-of-plane at a preferably thinner bridge $20_p$ between two nodes 22. The bending system 100 includes first and second benders 102, 104, each of preferably like structure and assembly. With respect to bender 102, the benders each include a first type of clamp bracket 110 and a handle 112. The first type of clamp bracket 110 includes a body 114, an upper threaded hole 117 defined in the body 114, and a pair of spaced-apart arms 116 descending from the body, which each terminate in an inwardly directed seat 118. A space 120 is defined between the seats 118 at the lower ends of the arms 116. The threaded hole 117 has an axis that extends into the body 114 at a transverse angle relative to the extension of the arms 116 from the body 114 and a lower surface of the arms. Referring to FIGS. 13 through 15, the space 120 between the seats 118 is sufficient to be received vertically over a bridge 22*p* of the plate but too small to accommodate vertical passage over the wings 28 of an adjacent node. However, the space 120 between the arms and above the seats 118 is sized to allow the arms to be moved along an axis, e.g., $A_b$ from a bridge 22*p* to an adjacent node 20. The handle 112 includes a proximal shaft 130 rotatably fixed to a distal threaded clamping bolt 132, which is threadedly coupled within the upper threaded hole 117 of the bracket 110 and can be advanced toward (or away from) the seats 118 by rotation (or counter-rotation) of the handle 112 relative to the bracket 110. The end 134 of the clamping bolt 132 is convex and sized to seat against the countersink 32 of a threaded screw hole 24. In a closed clamping position, the handle 112 preferably extends at a transverse angle relative to an axis of the threaded screw hole 24, but may alternatively extend at a 90° angle.

In use, an appropriate sized plate 10 is selected for a bone, such as a long bone or the pelvis. The orientation of the plate 10 is selected such that one of the first and second sides 16, 18 is identified for placement against the bone. The plate is then reshaped, as necessary, and secured to the bone. The plate may be fully or partially reshaped before any attachment to the bone, or may be preliminarily attached to the bone, e.g., via a compression screw at a elongate slot 26, or one or more locking screws at screw holes 24, and then reshaped to accommodate the anatomical contours of the bone. The plate is then further secured with compression screws or fixed angle screws at the threaded holes 24.

Figure 16A:
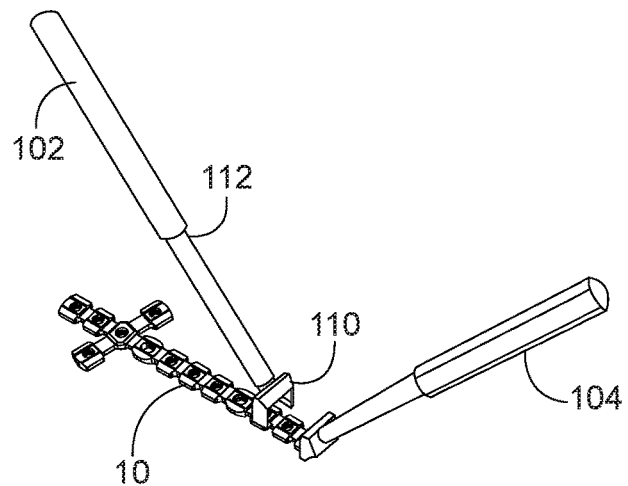
Figure 16B:
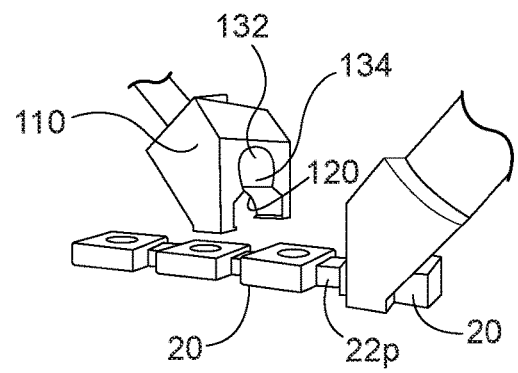
Figure 17A:
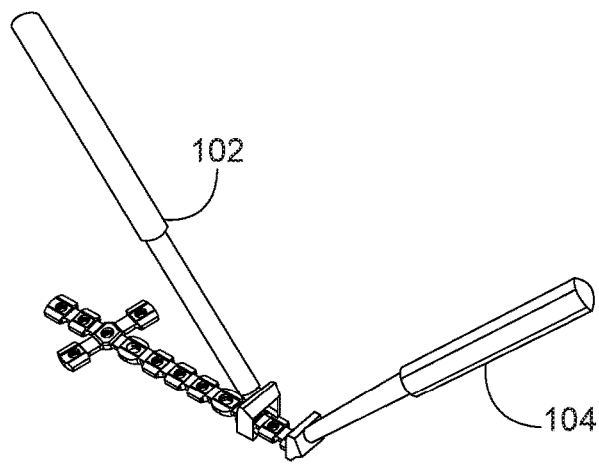
Figure 17B:
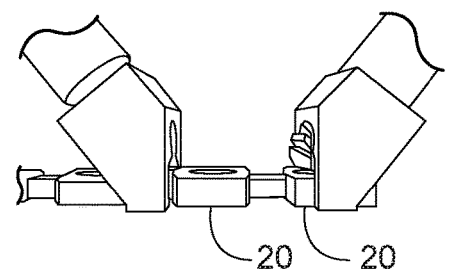
Figure 20A:
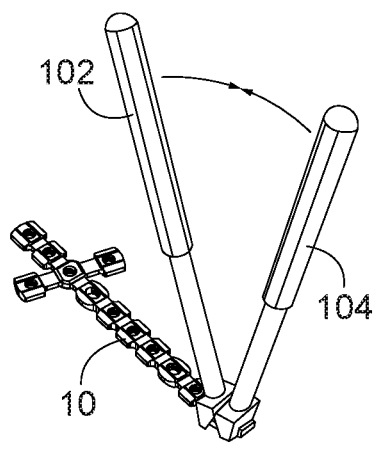
Figure 20B:
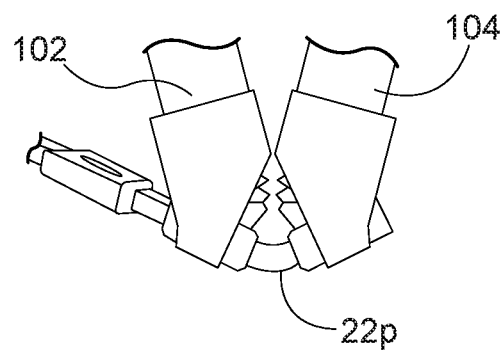

More particularly, to reshape the plate 10 at, for example, a bridge 22*p*, the pair of benders 102, 104 are positioned on the plate at two nodes 20 on opposite sides of the bridge 22*p* of plate 10. (FIGS. 16A and 16B) (It is appreciated that bridges 22*c* can also be bent, though they are more rigid than bridges 22*p*.) The two nodes at which the pair of benders 102, 104 are coupled may be consecutive nodes directly in contact with bridge 22*p*, or may be spaced apart from bridge 22*p* by one or more other nodes. If necessary, for each bender, the handle 112 is counter-rotated relative to the clamping bracket 110 to partially withdraw the end 134 of the clamping bolt 132 from the space 120 in clamping bracket 110 until sufficient clearance is provided within the space for accommodating the thickness of the node 20. The benders are adapted for use on all of the sizes of the plates in the sets 90, 290. Each bender 102, 104 is placed over a bridge (FIGS. 17A and 17B) and then longitudinally slid into place onto its respective node 20 (FIGS. 18A and 18B). The seats 118 at the ends of the arms 116 are able to grab under the wings 28 (elevated off the bone due to their taper), even when the plate 10 is seated on bone. Then the handle is rotated relative to the bracket to advance the end 134 of the clamping bolt 132 against the upper surface (e.g., first side 116) of the plate at the countersink 32. It is appreciated that when the handle 112 is rotated, the clamping bracket 110 is stably maintained in position on the plate by the engagement of the arms 116 about the wings 28 of the node. The handle 112 is rotated until the plate is clamped between the end 134 of the clamping bolt 132 and the seats 118 on the arms. The bolt 132 is sized to seat on the countersink 32 and not enter the threaded screw hole 24 (FIG. 3). Thus, the end 134 of the bolt cannot deform the threads of the screw hole 24. When the bolt 132 is tightened against the plate 10, the end 134 of the bolt on one side of the plate and the seats 118 at the opposite side of the plate provide three points of contact against the plate for stably gripping the plate. Once each bender 102, 104 is stably coupled to its respective node, a relative force is applied between the benders to deform the bridge $22_p$ therebetween and thereby shape the plate 10 (FIGS. 20A and 20B).

Figure 30:
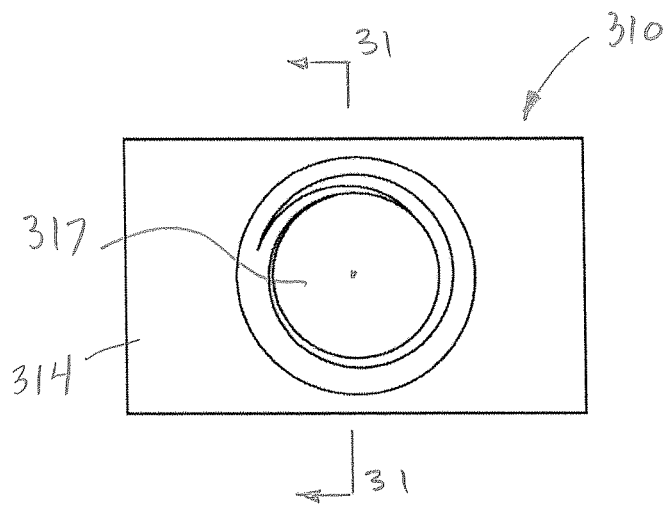
FIG. 30 is a top view of a clamping bracket of the system.
Figure 31:
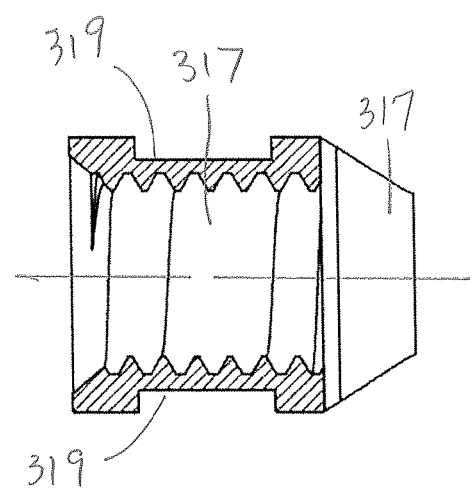
FIG. 31 is a section view across line 31-31 in FIG. 30.
Figure 32:
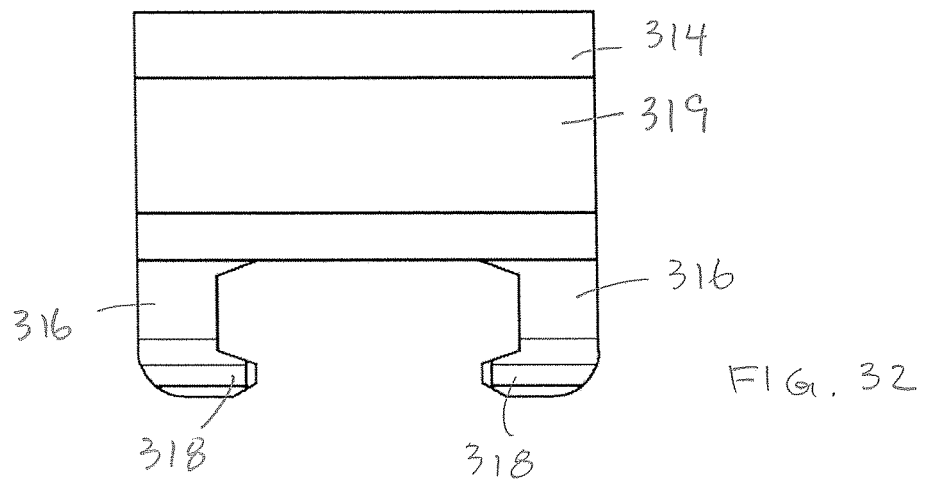
FIG. 32 is a side elevation view of the clamping bracket of FIG. 30.
Figure 33:
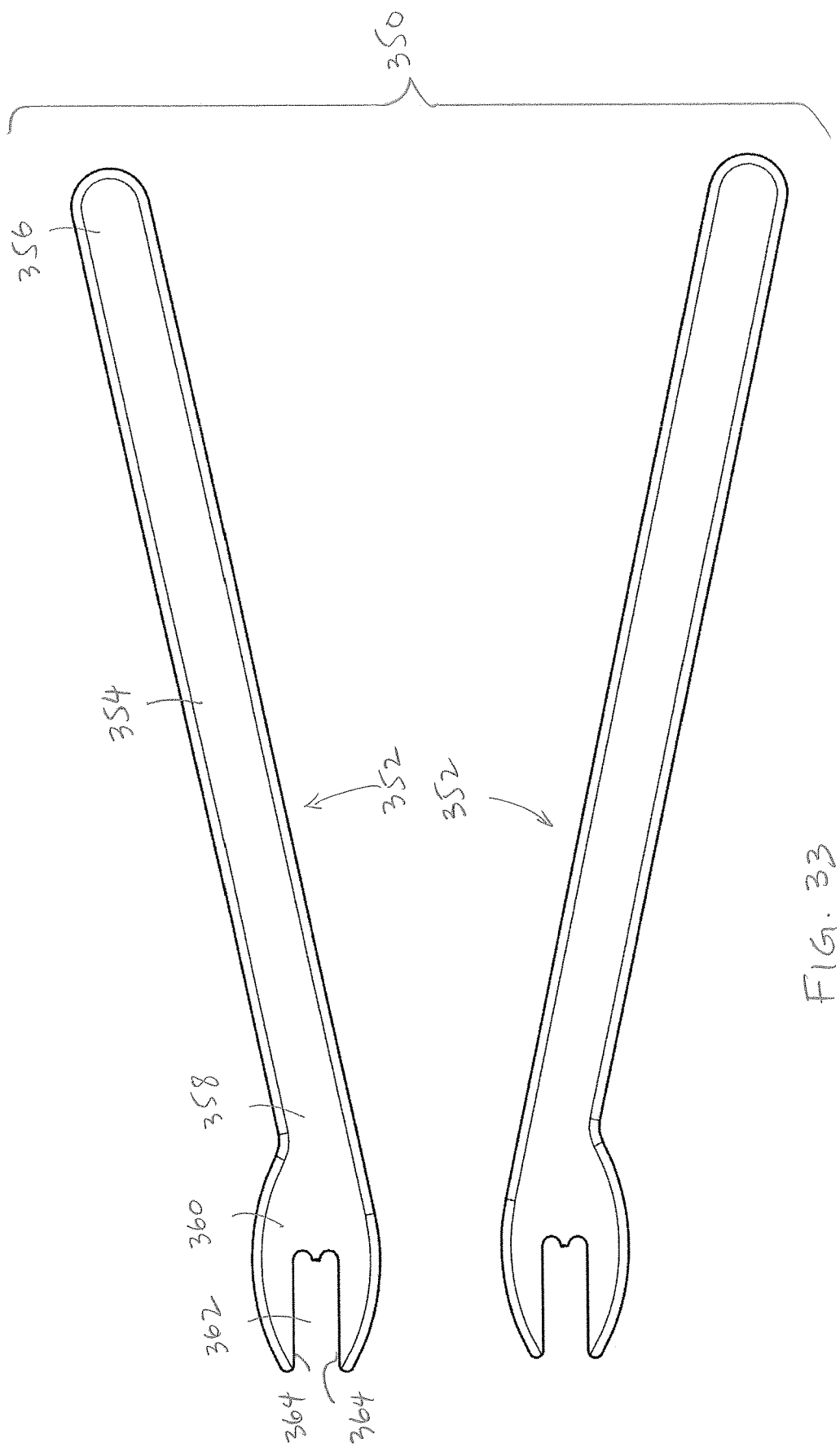
FIG. 33 is a plan view of a second pair of plate benders of the system.

Turning now to FIGS. 30 through 32, the bending system 100 may also be adapted to bend a plate "in plane". For such bending, the bending system 100 further includes second type clamp brackets 310. The clamping brackets 310 each include a body 314, a pair of spaced-apart arms 316 descending from the body, each arm 316 terminating in an inwardly directed seat 318, and an upper threaded hole 317 defined in the body 314, all similar to the first type of clamp bracket. However, in distinction, the threaded hole 317 has a central axis extending between and parallel to the extension of the arms 316 and the sides of the body 314. Further, parallel sides of the body transverse to the arms 316 are provided with recessed, parallel channels 319. Referring now to FIG. 33, in association with clamping brackets 310, the bending system also includes a pair 350 of reversible flat bending irons 352. Each bending iron 352 includes a handle 354 having a proximal end 356 and a distal end 358, and a flat head 360 extending at an oblique angle from the distal end 358. The head 360 includes an open mouth 362 with parallel sides 364 configured to stably engage within the parallel channels 319 of the clamping bracket 310.

Figure 34:
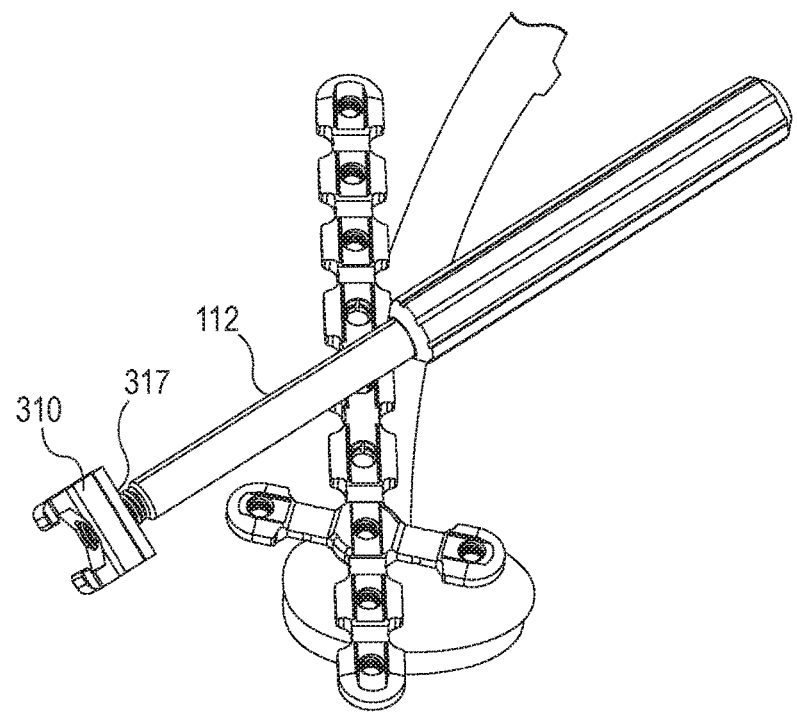
FIGS. 34 through 43 illustrate another method of bending plates of the system.
Figure 35:
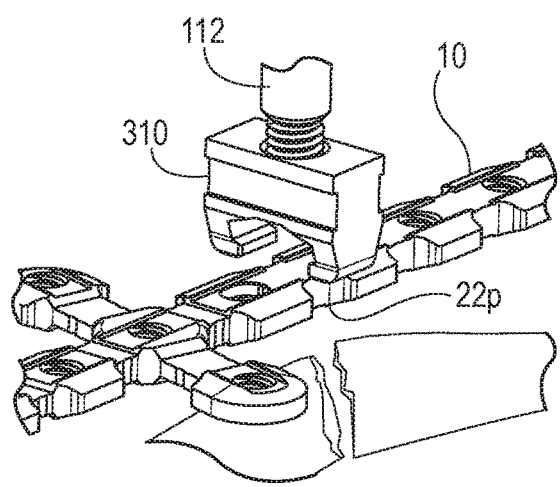
Figure 36:
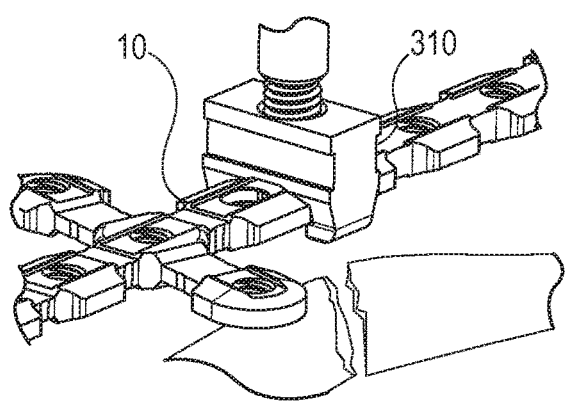
Figure 37:
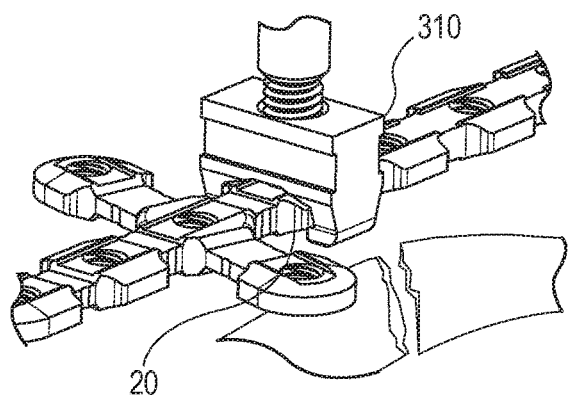
Figure 38:
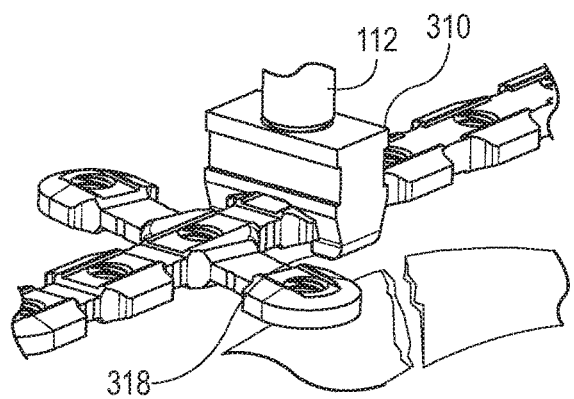
Figure 39:
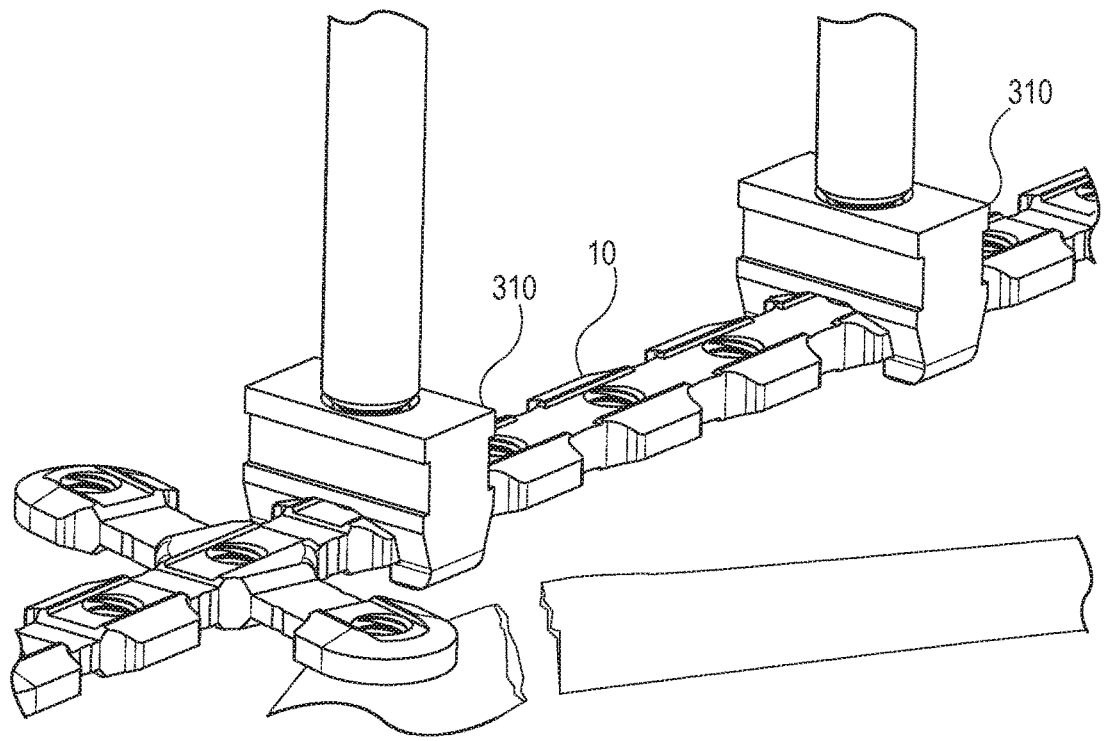
Figure 40:
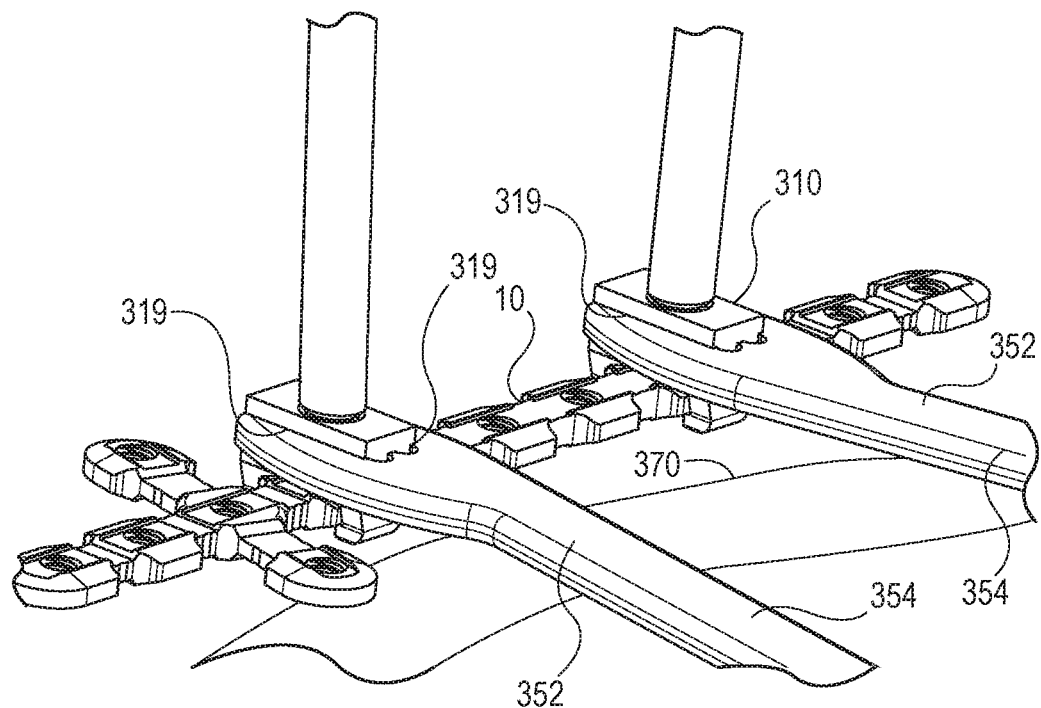
Figure 41:
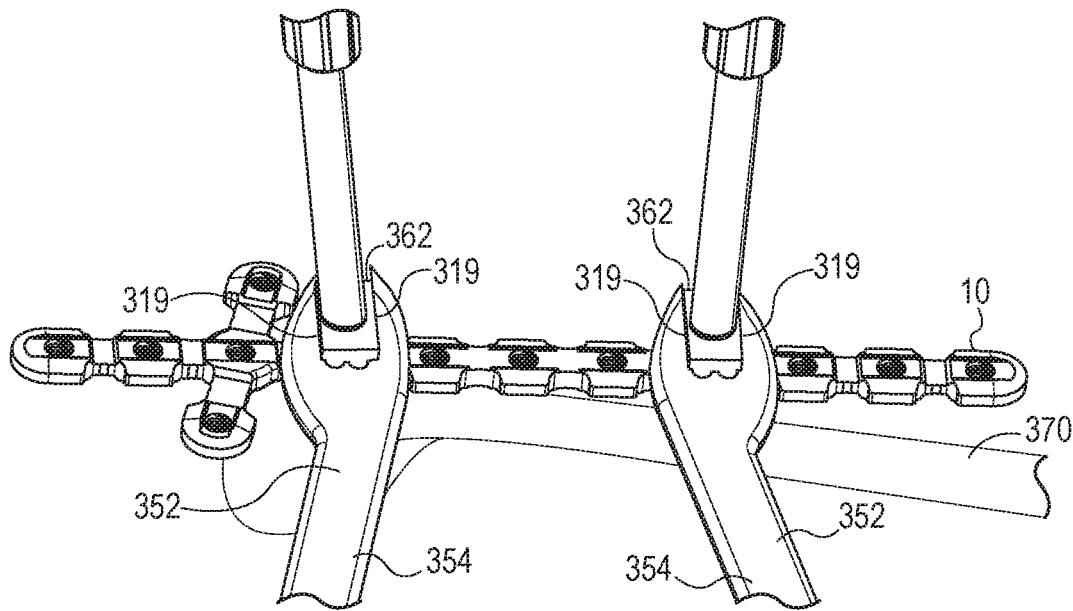
Figure 42:
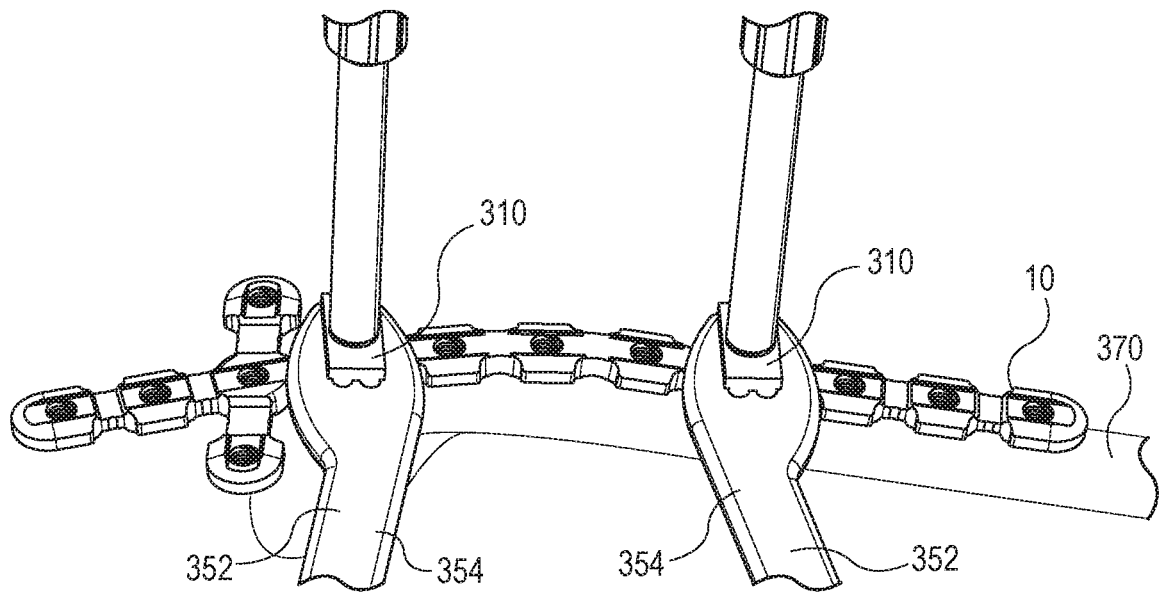
Figure 43:
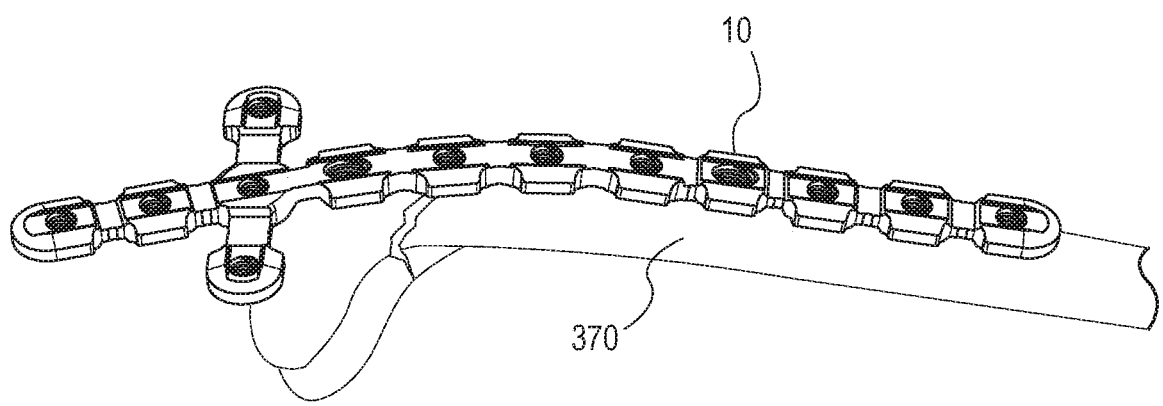

Turning to FIGS. 34 through 43, in use, handle 112 is partially inserted into the threaded hole 317 of the second-type clamp bracket 310 to engage the two components together (FIG. 34). The user then manipulates the handle 112 to advance the clamp bracket 310 onto the plate 10 at a bridge 22*p* (FIGS. 35-36), and then displace the clamp bracket 310 onto a node 20 (FIG. 37). The handle 112 is then rotated relative to the clamp bracket 310 to further advance the end 134 of the clamping bolt 132 (FIG. 12) into the hole 317 of the plate 10 to clamp the node 20 between the end 134 and the seats 318 of the clamp bracket 310 (FIG. 38). A second clamping bracket 310 is similarly advanced onto the plate 10 (FIG. 39). All of the above is generally as described above with respect to bracket 110. The mouths of the bending irons 352 are then coupled to the clamp brackets 310 at the channels 319, preferably with the bending iron handles 354 angled away from each other (FIGS. 40-41). An angular force is then applied to the proximal ends 356 (FIG. 33) of the bending iron handles 354 to displace the clamp brackets 310 relative to each other and consequently deform the plate 10 into alignment with the bone 370 (FIG. 42). The bending irons 352 and clamping brackets 310 are then removed from the plate 10, and the contour of the plate 10 relative to the bone 370 is assessed to determine whether the plate suitably conforms to the anatomy (FIG. 43).

While bending of the plate has been described using a pair of plate benders, the plate may also be bent using a single plate bender of the types described in conjunction with an alternate secondary plate stabilizer or bender. By way of example, the alternate secondary bender may comprise a shaft that threadedly couples to a node coaxial with a threaded screw hole. The shaft may threadedly engage the screw hole 24 to apply force to the node or maintain position of the node. Such an alternate bender may be preferred in circumstances where access to the bone does not readily permit use of the described benders.

Figure 21:
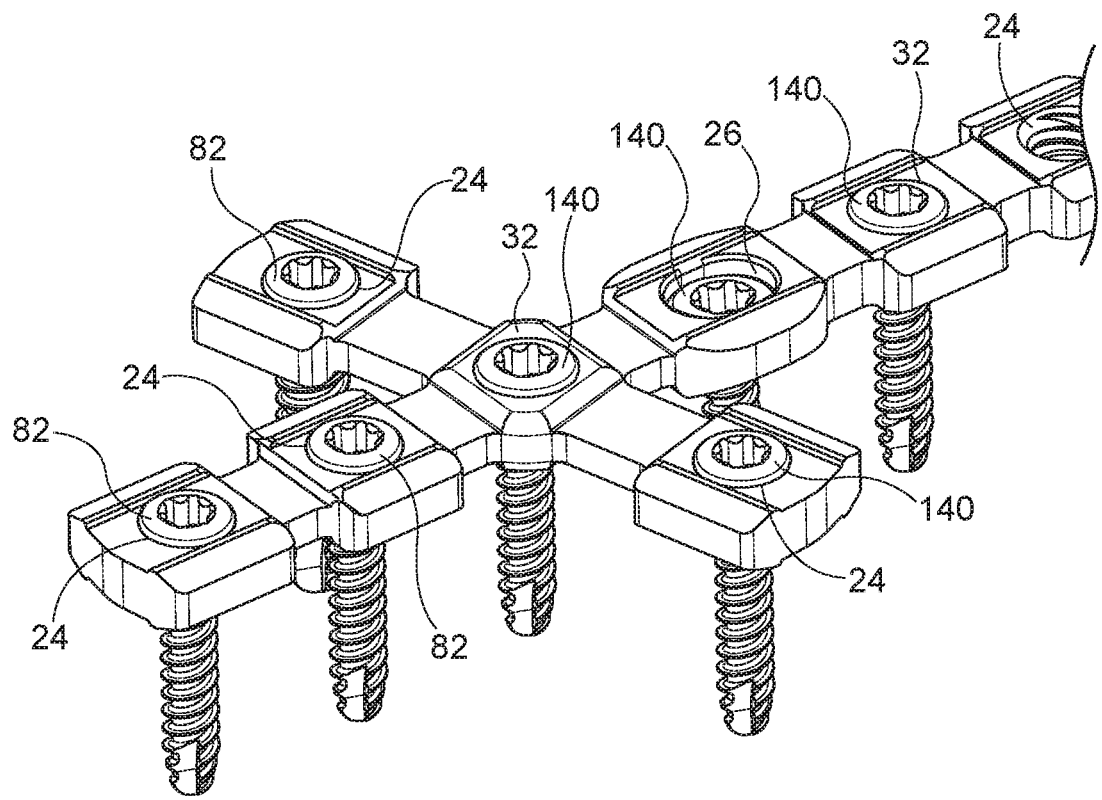
FIG. 21 is a broken perspective view of the system of a plate provided with screws.
Figure 7:
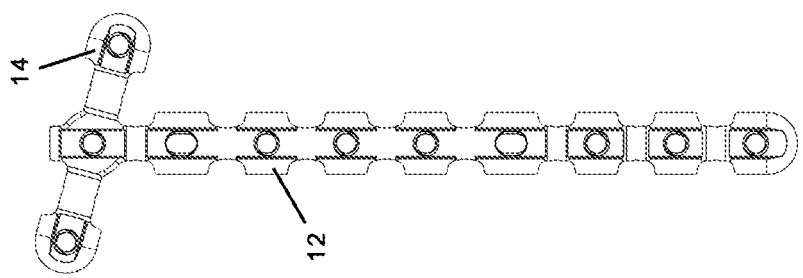
FIGS. 7 through 10 illustrate, in plan view, various exemplar shapes for a plate as shown in FIG. 1, with peripheral portions thereof removed.
Figure 8:
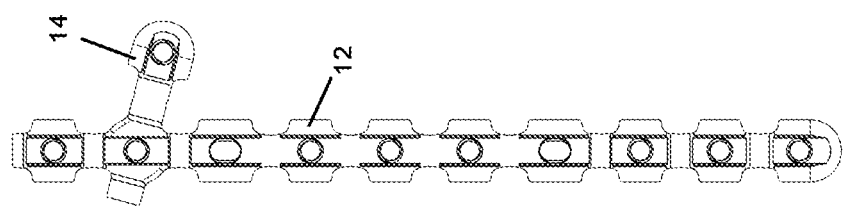
Figure 9:
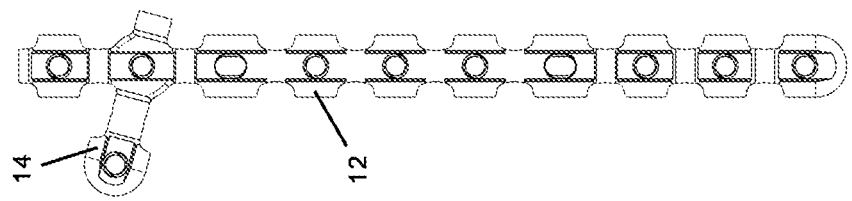

As shown in FIGS. 6 and 21, the system also includes screws for securing the plate to the bone. In a preferred system, both locking screws 82 and compression screws 140 are provided. In addition, screws of different diameter and length are also provided for appropriate fixation and repair of the bone injury. The threaded screw holes 24 are adapted to receive both of the locking screws 82 and compression screws 140. The locking screws 82 threadedly engage with the threaded screw holes 24. The compression screws 142 having a lower head surface that engages the countersink 32 above the threads of screw holes 24.

Figures 22A, 22B:
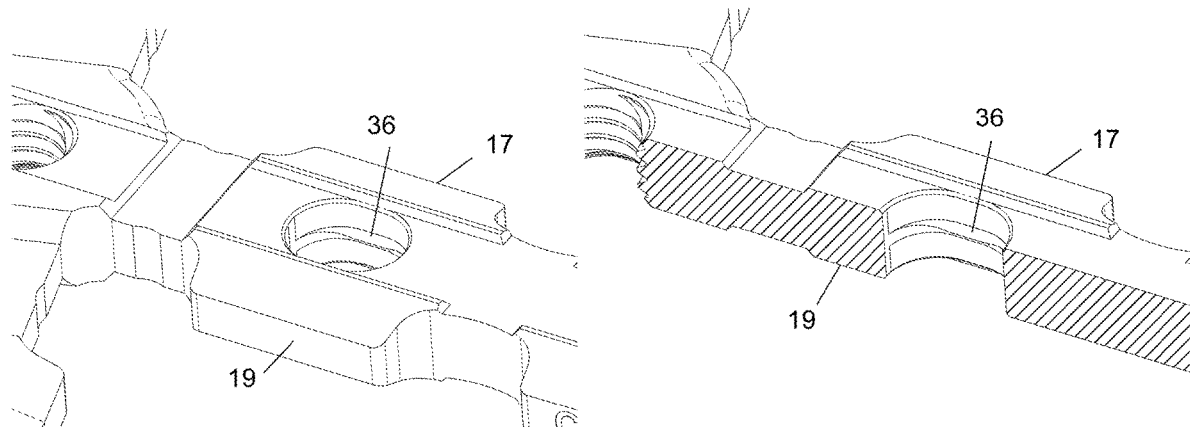
FIG. 22A is an enlarged perspective view of an elongate slot in the plate.
FIG. 22B is a view similar to FIG. 22A shown in longitudinal section.
Figure 23:
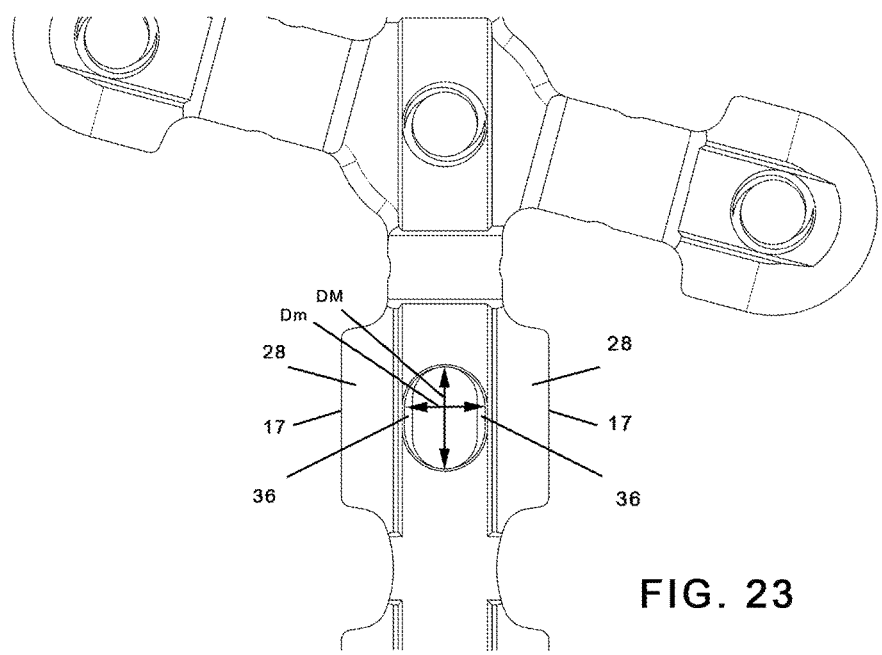
FIG. 23 is an enlarged partial plan view of a portion of the plate containing an elongate slot.

Turning now to FIGS. 22A, 22B and 23, the elongate screw holes or slots 26 have a major diameter $D_M$ and a minor diameter $D_m$. The slots include two thin ledges 36 extending along the long sides of the hole and parallel to the major diameter $D_M$. The ledges 36 have a thickness in the dimension extending between the first and second sides 16, 18, and parallel to the lateral sides 17, 19, of the plate. The ledges 36 taper toward the longitudinal axis of the plate at an angle. The ledges have a width in the lateral dimension. The ledges 36 are located recessed relative to each of the first and second sides 16, 18 of the plate, and more particularly located centrally between the first and second sides. As stated above, the wings 28 taper at a first angle.

Figure 24:
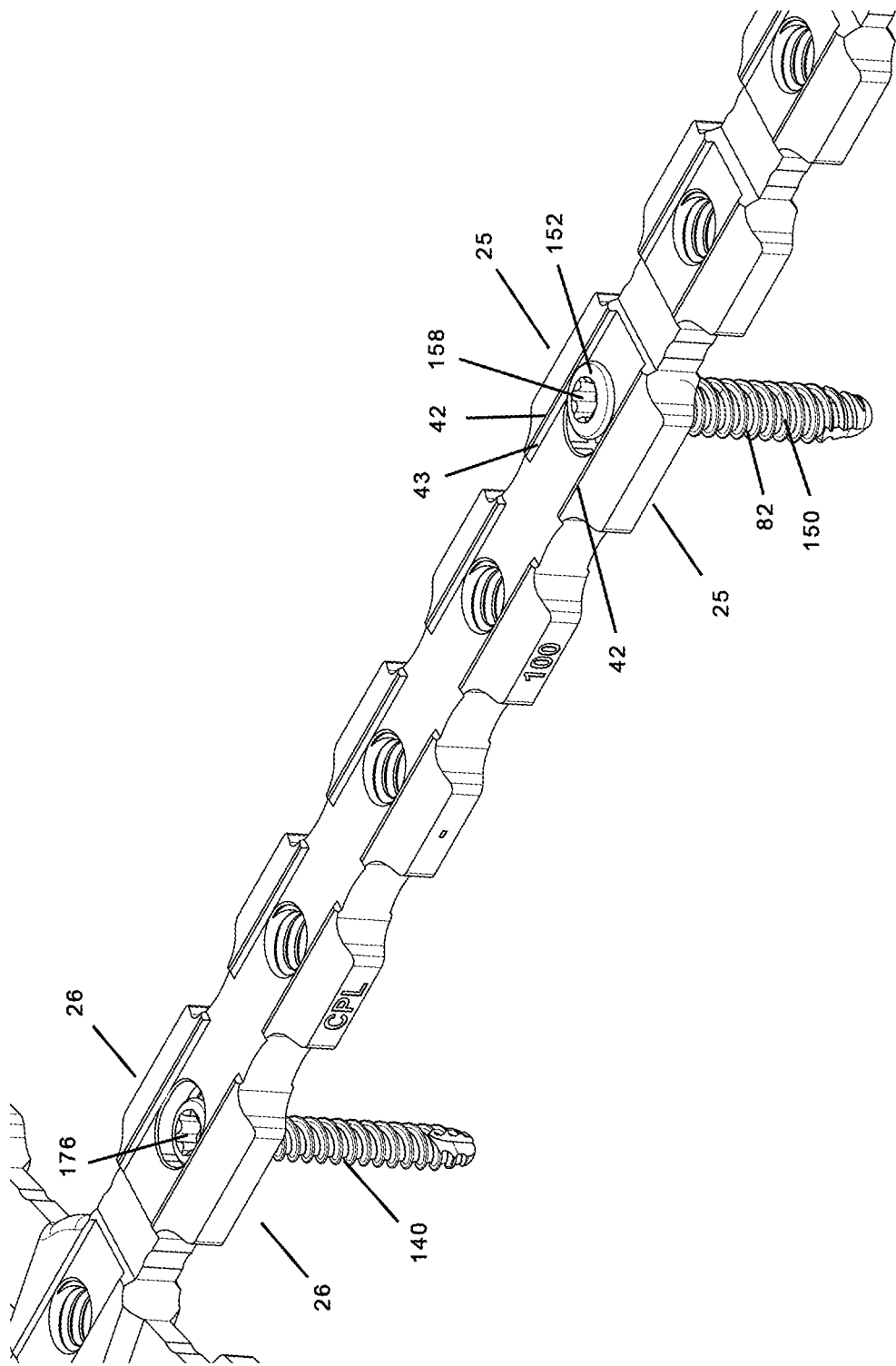
FIG. 24 is a partial perspective view of the bone plate showing a first elongate slot provided with a compression screw and a second elongate slot provided with a locking screw.
Figure 25:
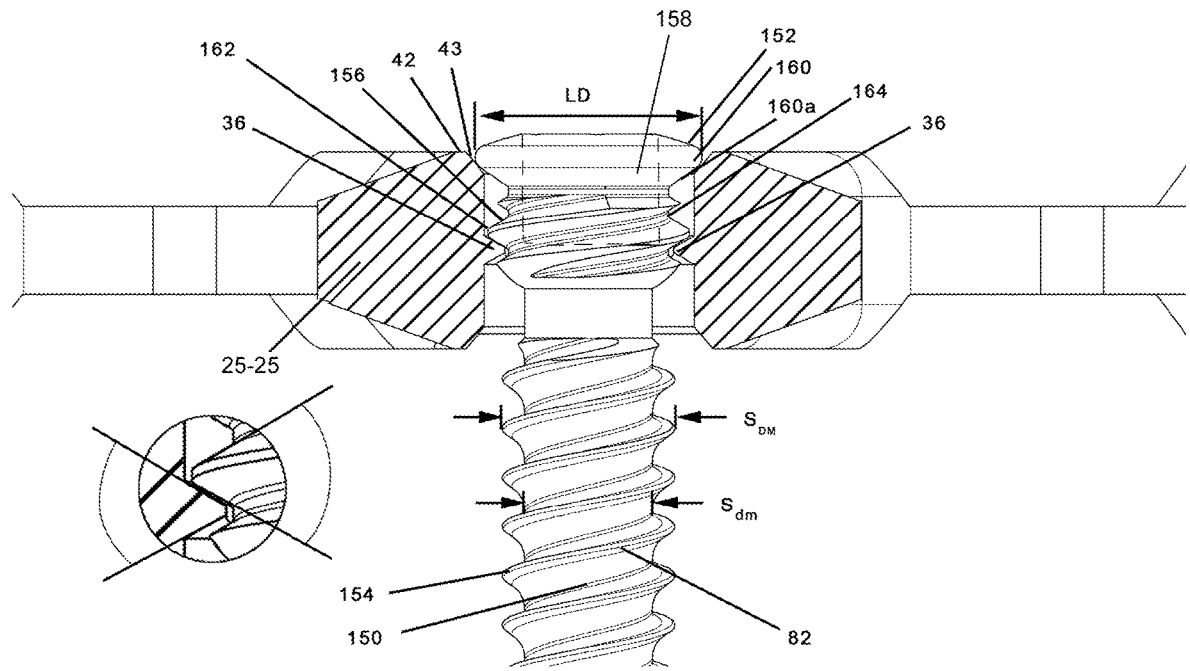
FIG. 25 is a cross-section across line 25-25 in FIG. 24.

Referring to FIGS. 24 and 25, the locking screws 82 each have a shaft 150 and a head 152. The shaft 150 includes bone-engaging threads 154 having a major diameter $S_{DM}$ and a minor diameter $S_{dm}$. The head 152 includes external threads 156, a driver slot 158 for receiving a driver, and an upper lip 160. The threads 156 define a first threaded pitch, a crest 162 (defining a major diameter $H_{DM}$), a root 164 (defining a minor diameter $H_{dm}$), and a thread angle between the crest 162 and the root 164. The thickness of the ledge 36 is less than the first thread pitch. The angle of taper of the ledge 36 is preferably substantially the same (±5°) as the thread angle between the crest 162 and root 164. The width of the ledge 36 is preferably approximate to, or slightly smaller than, the difference between the crest and root dimensions, or (major diameter−minor diameter)/2. The lip 160 has a diameter $L_D$ greater than the minor diameter $D_m$ of the elongate slot 26 (FIG. 23). The lower surface 160a of the lip 160 optionally extends at substantially a same angle (±5°) as the medial surfaces 43 of the rails 42. When the locking screw 82 is driven into the elongate slot 26, the ledge 36 functions as a single thread, and the threads on the head 156 threadedly engage the ledge. As such, the locking screw 82 is threadedly advanced into the plate relative to the ledge, and locked relative thereto. Also, the locking screw 82 can be advanced only until the lower surface of the lip 160 stops against the beveled medial surface 43 of the rail 42 laterally surrounding the slot, which forms a seat for the locking screw.

Figure 26:
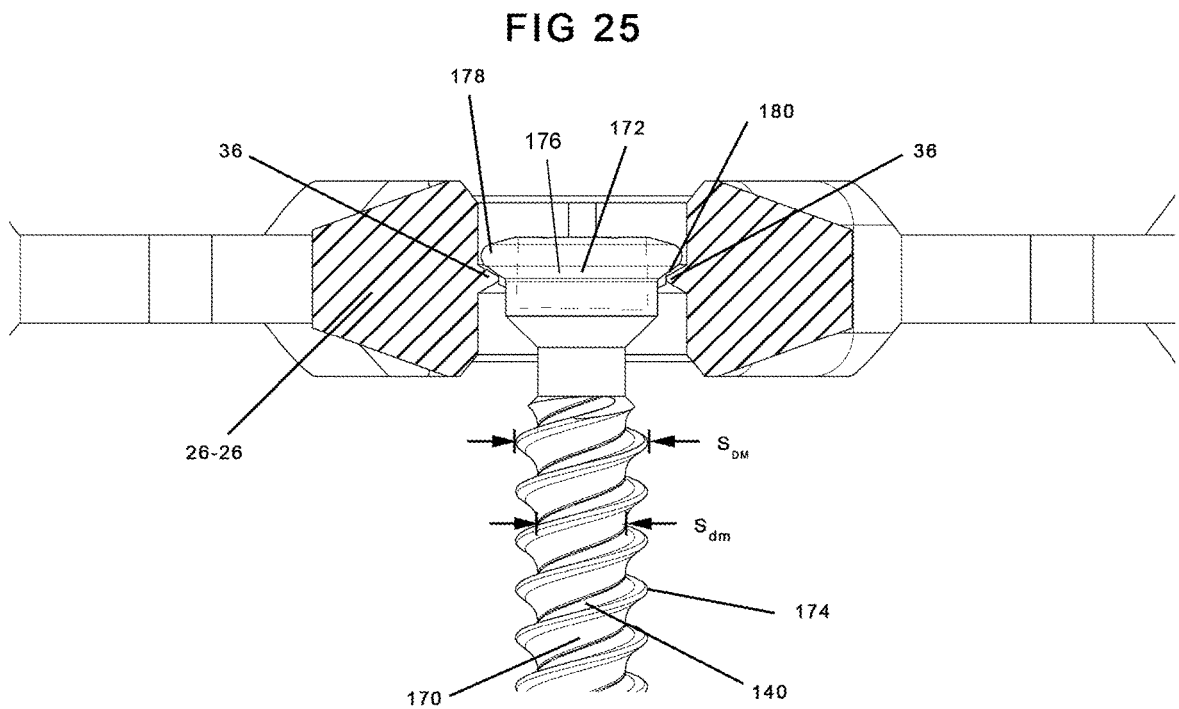
FIG. 26 is a cross-section across line 26-26 in FIG. 24.

Referring to FIGS. 24 and 26, the compression screws 140 each have a shaft 170 and a head 172. The shaft 170 includes bone-engaging threads 174 having a major diameter $S_{DM}$ and a minor diameter $S_{dm}$. The head 172 includes a driver slot 176 for receiving a rotational driver and an upper lip 178 that is smaller than a minor diameter of the slot 26 adjacent to, but not between, the ledges 36. The lower surface 180 of the lip 178 extends at an angle that preferably approximates the facing surface of the ledge 36. When the compression screw 140 is driven into the elongate slot 26, the ledge 36 functions as a stop which the lip 178 contacts in applying compression to the plate.

Figure 27:
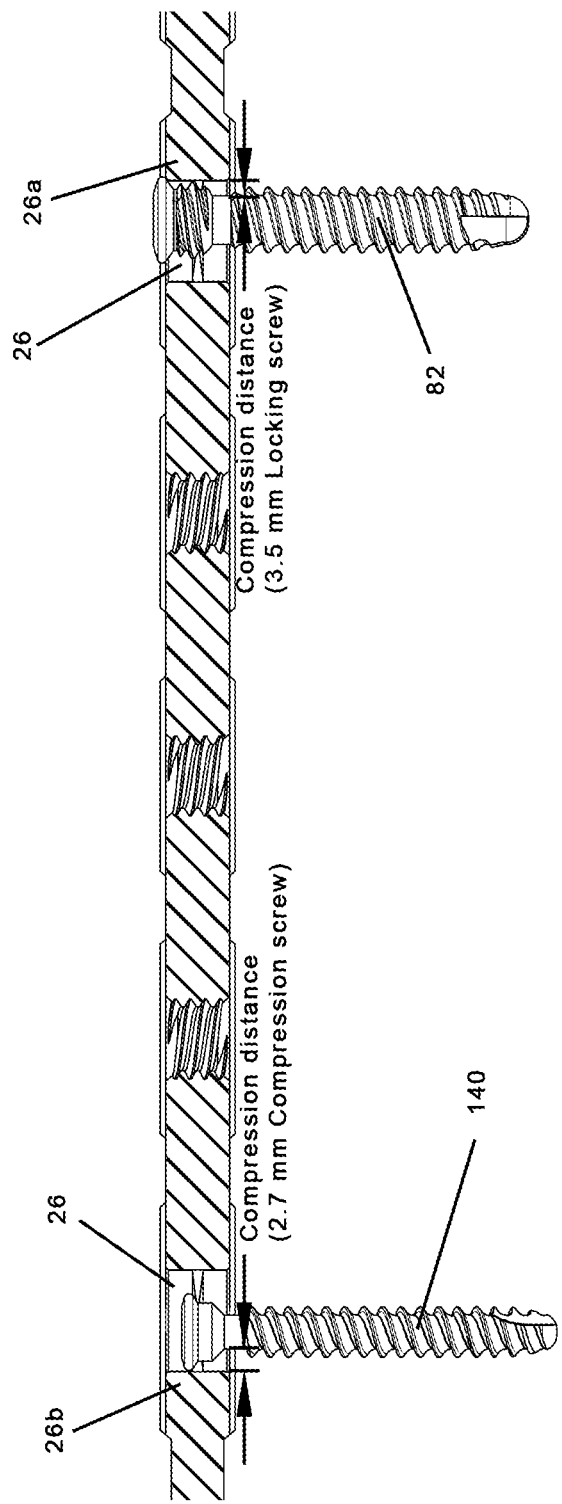
FIG. 27 is a longitudinal section view across the bone plate and screws shown in FIG. 24.

In addition, referring to FIGS. 24 and 27, each of the locking screw 82 and compression screw 140 are adapted to provide dynamic compression; i.e., longitudinal displacement across a fracture, as the respective screw is driven into a respective elongate slot 26. That is, when the screw is inserted at one end of the elongate slot, the head of the respective screw imparts a horizontal force component when driven vertically into contact against the plate. By way of example, locking screw 82 is inserted adjacent the end 26a of the slot in which displacement of the plate is intended. As the screw 82 is advanced toward a locking configuration with the plate, the head displaces the plate by up to a distance corresponding to (major diameter of the head thread−minor diameter of the shaft thread)/2. In one locking screw with a 3.5 mm shaft major diameter, the longitudinal displacement is (4.1 mm−2.6 mm)/2=0.75 mm. To effect dynamic compression with the compression screw 140, the screw is also inserted adjacent an end 26b of the slot in which displacement of the plate is intended. As the screw is advanced into compression against the plate, the head displaces the plate by up to a distance corresponding to (diameter of the lip at the head−minor diameter of the shaft thread)/2. In one compression screw with a 2.7 mm shaft major diameter, the longitudinal displacement is (4.1 mm−2.1 mm)/2=1.0 mm. As such, in the described set of locking screw and compression screw, the locking screw effects 75% of the longitudinal compression of the compression screw; this result is at the median of a preferred relationship (75%±15%, or 60%-90%) of the relative longitudinal, or dynamic, compression between the two types of screws.

Figure 48:
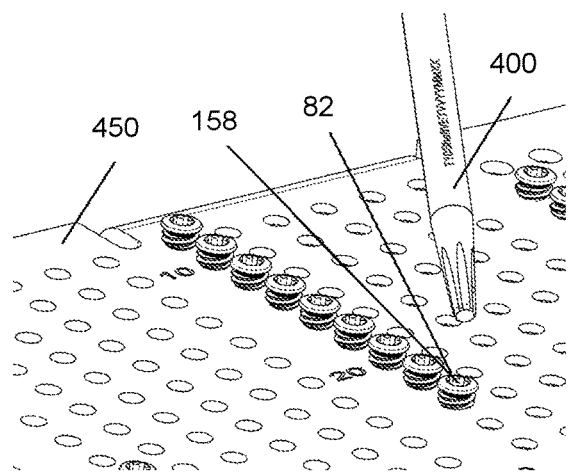
FIGS. 48 through 50 illustrate a method of using the screw driver to pick up screws from a tray containing screws.
Figure 49:
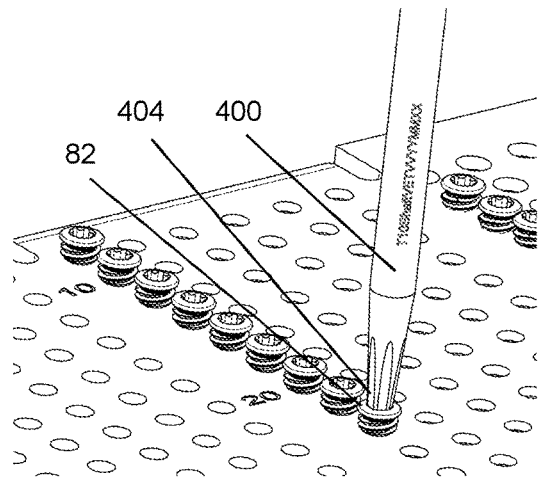
Figure 50:
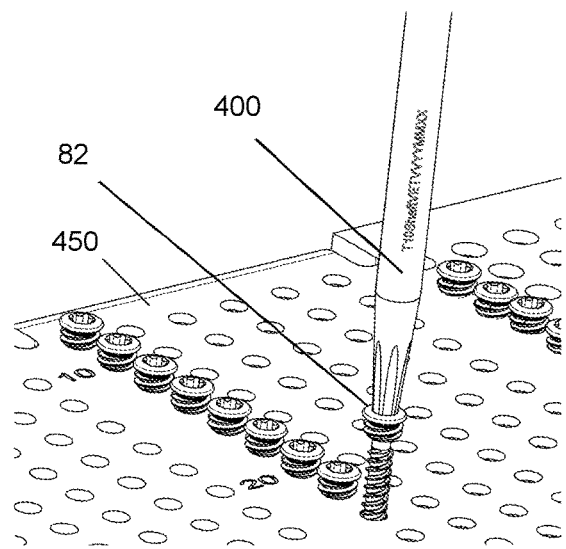

Turning now to FIGS. 44 through 46, a screw driver 400 for picking up the screws 82, 140 and driving the screws through the screw holes 24, 26 and into the bone is provided. The screw driver 400 includes a shaft 402 having a distal T10 torx (hexalobe) head 404 and a proximal end 406. The head 404 includes inner lobes 410 and outer lobes 412. The inner lobes 410 define a short (0.8 mm) distal portion 410a of straight milled grooves which continue into a proximal portion 410b of curved milled grooved (R=~38 mm). The short distal portion 410a aligns with the corresponding socket 158 in the screw 82, thus providing directionability. In distinction from a conventional hexalobe driver, the outer lobes 412 are not curved. Rather, the head 404 is turned on a lathe to define a 4.5 degree cone 418 that intersects the milled grooves 416 of the inner lobes 410. The cone 418 provides a combination of proper friction and good control of the tip length. Conventional friction angles of 3 degrees were found to provide too much variability to the length of the head that extends into the screw socket 158. This leads to the head 404 bottoming out within the screw socket with insufficient frictional engagement between the lobes 410, 412 of the head 404 and the socket 158 of the screw. Alternatively, with the head sitting too high in the socket, too little engagement is made between the inner and outer lobes 410, 412 and the socket 158 and there exists an associated potential for stripping the screw as a torque is applied. Also, both of these improper fits can result in tilt of the driver head 404 relative to the socket, and a lack of directionality. The actual frictional engagement between the head 404 and the screw socket results from the edges between the cone 418 and the grooves 410a, 410b, with such edges digging into a transition zone between the inner and outer corners of the socket 158 of the screw 82. This creates a high friction interface for engaging the screw. Referring to FIGS. 48 and 49, the head 404 is designed to self-orient axially into the screw socket 158 of screw 82 to a correct depth so that it does not alter the alignment (and thus the "directionability") of the screw 82 and has stability in the screw socket 158. In addition, the driver head 404 is configured and engages the screw socket 158 at a correct depth for generating a frictional engagement which allows the head 404 to pick up and withdraw the screw 82 from an array of screws in a tray 450, and also is adapted to apply significant torque to the screw 82 to insert the screw into bone (FIGS. 49-50). The use of driver head 404 to pick up and drive screw 82 is equally applicable to screw 140.

Turning back to FIGS. 44 and 45, an industry standard AO connector is provided to the proximal end 406 of the shaft 402 includes. The AO connector 406 includes a longitudinal flat 420 at one side and a peripheral groove 422 at its opposite side. In distinction from a standard AO connector, the proximal end 406 includes a threaded set screw hole 424 extending into the flat 420. With such structure, the shaft 402 can be positioned as a driver bit in powered driver with a mating AO socket structure. In addition, a handle 426 including a lateral hole 428 aligned with the set screw hole 424 can be assembled onto the same shaft, and secured to the shaft with a set screw 430 that engages the set screw hole 424. This permits the driver to be hand-operated. Thus no pressing, over molding or cross-pining is required for the connection to a permanent (or semi-permanent) handle.

The system provides a single plate design that accommodates left and right anatomies and which can also be customized in shape via removal of one or more nodes and bending along one or more bridges. The single plate design is readily adaptable into treatment even for those surgeons who have not had significant prior experience with anatomical or shapeable plates adapted for specific bones.

There have been described and illustrated herein several embodiments of a bone plate system including bone plates, plate benders, and screws, and methods of implanting the plate in bones of a mammal. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A bone plate for repair of a bone, consisting of:
a planar metal plate consisting of a first side, an opposite second side, and a plurality of nodes and intervening bridges extending in a linear arrangement,
the plurality of nodes having a longitudinal channel at each of the first and second sides of the plate, rails extending longitudinally along the longitudinal channels at each of the first and second sides of the plate, a countersunk screw hole countersunk between and relative to the rails at each of the first and second sides of the plate, and bilaterally extending wings that laterally taper in thickness, and
the bridges having a reduced area moment of inertia relative to the nodes such that the bridges have an increased propensity to bending relative to the nodes when a force is applied thereto,
wherein the first and second sides of the plate have a same structure such that each of the first and second sides are configured to be positioned against and in contact with the bone.

2. The bone plate according to claim 1, wherein:
a plurality of the nodes have threaded circular holes, and
a plurality of the nodes have non-circular holes.

3. The bone plate according to claim 1, wherein:
the plate is straight.

4. A bone plate configured for use with screws and for repair of a bone, consisting of:
a metal plate having a first side, a second side, exactly thirteen nodes, and intervening bridges between the thirteen nodes, wherein, in order,
a first node has a threaded circular hole,
a second node has a non-circular hole,
third and fourth nodes have threaded circular holes,
a fifth node has a non-circular hole,
sixth, seventh, and eighth nodes have threaded circular holes,
a ninth node has a non-circular hole,
tenth and eleventh nodes have threaded circular holes,
a twelfth node has a non-circular hole, and
a thirteenth node has a threaded circular hole,
each of the threaded circular holes having a common size and structure for receiving screws with threaded heads, and each of the non-circular holes having a common size and structure for receiving screws with non-threaded heads, and
the bridges having a reduced area moment of inertia relative to the nodes such that the bridges have an increased propensity to bending relative to the nodes when a force is applied thereto.

5. The bone plate according to claim 4, wherein:
the plate is adapted such that when a sufficient bending force is applied at the bridge located between the sixth and seventh nodes, the plate breaks into two plate portions,
a first plate portion having four nodes with threaded circular holes and two nodes with non-circular holes, and
a second plate portion having five nodes with threaded circular holes and two nodes with non-circular holes,
wherein each of the first and second plate portions is suitable for use on the bone.

6. The bone plate according to claim 4, wherein:
the plate is planar.

7. The bone plate according to claim 4, wherein:
the plate is straight.

8. The bone plate according to claim 4, wherein:
the first and second sides of the plate have a same structure such that each of the first and second sides are configured to be positioned against and in contact with the bone.

9. The bone plate according to claim 4, wherein:
each node has laterally tapered wings.

10. The bone plate according to claim 4, wherein:
each node has a central longitudinal channel.

11. The bone plate according to claim 4, wherein:
the thirteen nodes each have a longitudinal channel, rails extending longitudinally along the longitudinal channel, a countersunk screw hole between the rails, and bilaterally extending wings that laterally taper in thickness.

12. A kit of bone plates for repair of bones, comprising:
a first plurality of planar metal plates, each of a common shape but of a different size, each consisting of a first side, an opposite second side, and a plurality of nodes and intervening bridges extending in a linear arrangement,
the nodes each having a longitudinal channel, rails extending longitudinally along the longitudinal channel, a countersunk screw hole between the rails, and bilaterally extending wings that laterally taper in thickness, and
the bridges having a reduced area moment of inertia relative to the nodes such that the bridges have an increased propensity to bending relative to the nodes when a force is applied thereto,
wherein each of the first and second sides of the plate have a same surface structure such that each of the first and second sides are configured to be positioned against and into contact with a bone.

13. The kit of bone plates of claim 12, further comprising:
a second plurality of planar metal plates, each of a common shape but of a different size, each consisting of a straight body portion and a cross-arm extending transverse to the straight body portion at a non-orthogonal angle, the straight body portion and cross-arm defining a first side, an opposite second side, and a plurality of nodes and intervening bridges,
each node having a longitudinal channel, rails extending longitudinally along the longitudinal channel, a countersunk screw hole between the rails, and bilaterally extending wings that laterally taper in thickness, and
each bridge having a reduced area moment of inertia relative to surrounding nodes such that the bridges have an increased propensity to bending relative to the nodes when a force is applied thereto.

* * * * *